(12) United States Patent
Johnson et al.

(10) Patent No.: US 6,679,529 B2
(45) Date of Patent: Jan. 20, 2004

(54) CONNECTION SYSTEM

(76) Inventors: Theodore D. Johnson, 2219 Glenmoor Rd. South, Clearwater, FL (US) 34624-4922; Robin M. Boley-Johnson, 2219 Glenmoor Rd. South, Clearwater, FL (US) 34624-4922

( * ) Notice: Subject to any disclaimer, the term of this patent is extended or adjusted under 35 U.S.C. 154(b) by 145 days.

(21) Appl. No.: 09/682,202

(22) Filed: Aug. 6, 2001

(65) Prior Publication Data

US 2003/0030272 A1 Feb. 13, 2003

(51) Int. Cl.⁷ .................... A61M 39/00; F16L 35/00
(52) U.S. Cl. .................... 285/423; 285/915; 285/3; 604/905
(58) Field of Search .................... 285/915, 423, 285/2, 3, 914, 4; 604/905

(56) References Cited

U.S. PATENT DOCUMENTS

| | | |
|---|---|---|
| 3,865,411 A | 2/1975 | Rowe et al. |
| 4,019,512 A | 4/1977 | Tenczar |
| 4,022,205 A | 5/1977 | Tenczar |
| 4,030,494 A | 6/1977 | Tenczar |
| 4,149,534 A | 4/1979 | Tenczar |
| 4,418,945 A | 12/1983 | Kellogg |
| 4,619,640 A * | 10/1986 | Potolsky et al. ............ 604/905 |
| 4,731,061 A | 3/1988 | Matkovich |
| 5,104,390 A * | 4/1992 | Yum et al. .................. 604/323 |
| 5,393,101 A | 2/1995 | Matkovich |
| 5,810,398 A | 9/1998 | Matkovich |
| 5,868,433 A | 2/1999 | Matkovich |
| 5,989,240 A * | 11/1999 | Strowe ....................... 604/905 |
| 6,341,802 B1 | 1/2002 | Matkovich |
| 2002/0093192 A1 | 7/2002 | Matkovich |

* cited by examiner

Primary Examiner—David Bochna
(74) Attorney, Agent, or Firm—Anton J. Hopen; Smith & Hopen, P.A.

(57) ABSTRACT

An apparatus for establishing aseptic/sterile connections including a substantially flexible, substantially transparent sterile barrier enclosing a terminal end of a conduit and a resilient, deformable support card which further includes an adhesive perimeter covered by a release paper and a rolling membrane with a continuous, removable, yieldable, flexible strip material. A portion of the rolling membrane is removably adhered to the support card and overlies the end of the conduit. A force applied to the free end of the rolling membrane withdraws the entire rolling membrane to expose the end of the conduit so that an aseptic/sterile connection is achieved by adhering opposing support cards together, removing the rolling membrane to create a sterile corridor between a first sterile barrier and a second sterile barrier, and mating the terminal end of a first conduit and a second conduit together.

23 Claims, 20 Drawing Sheets

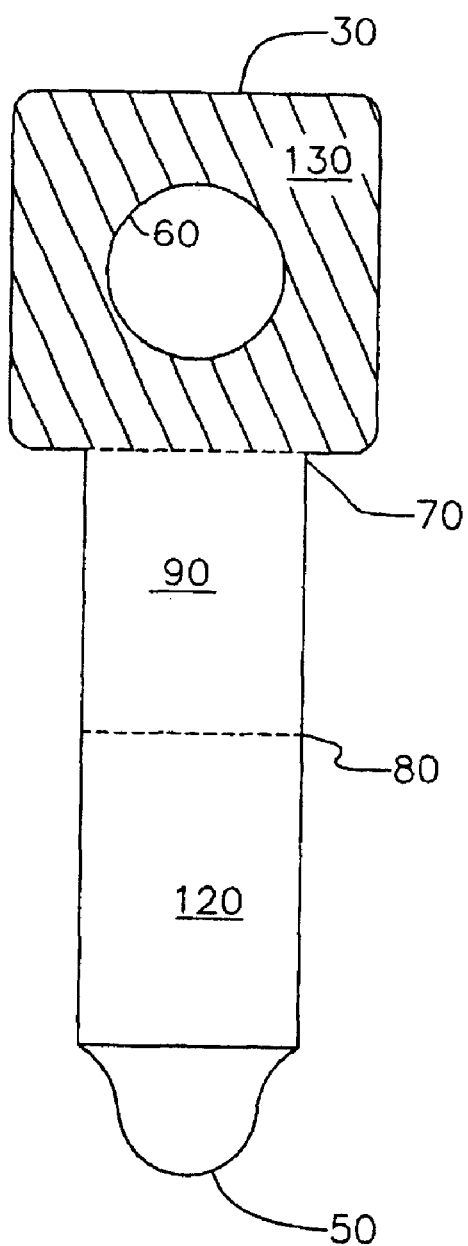
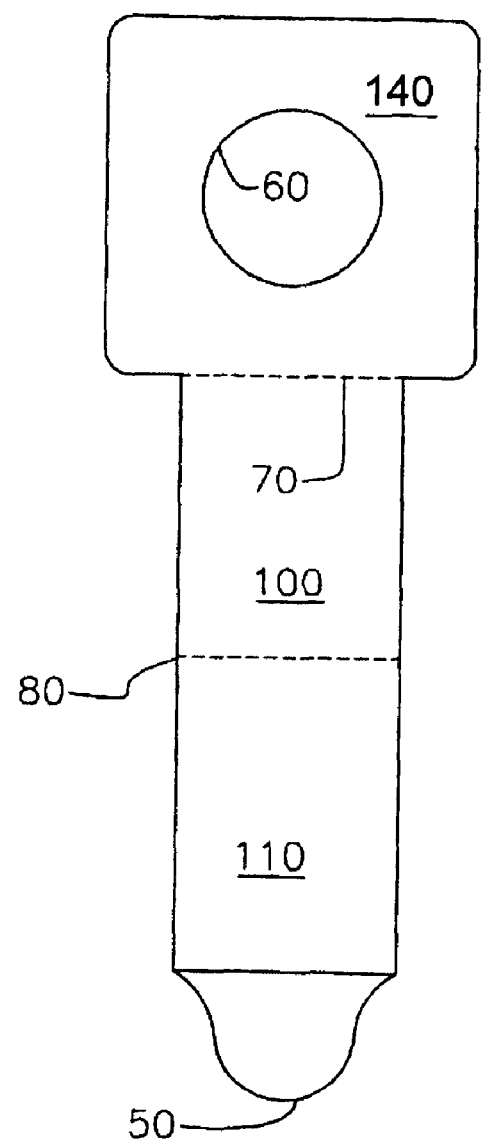

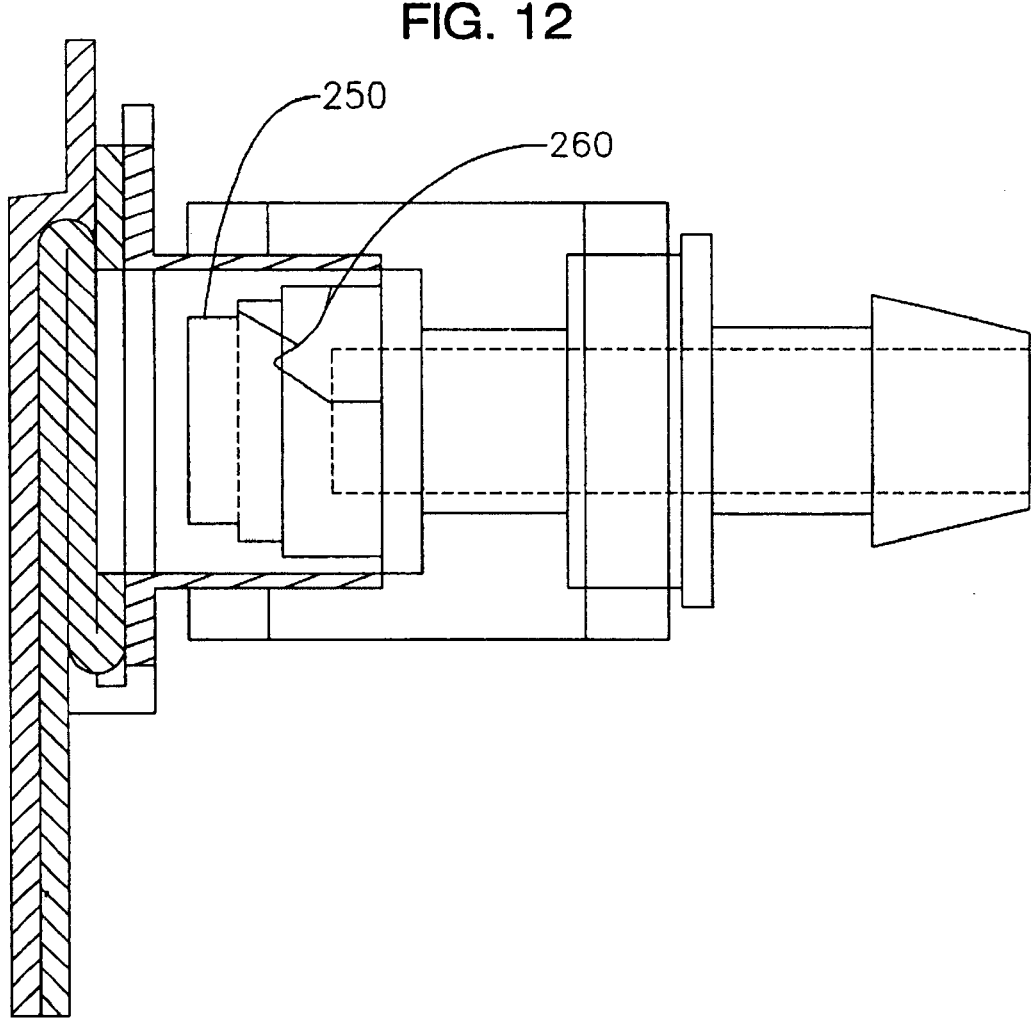

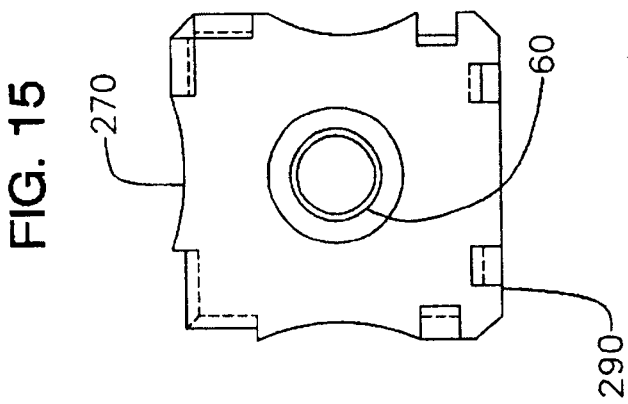
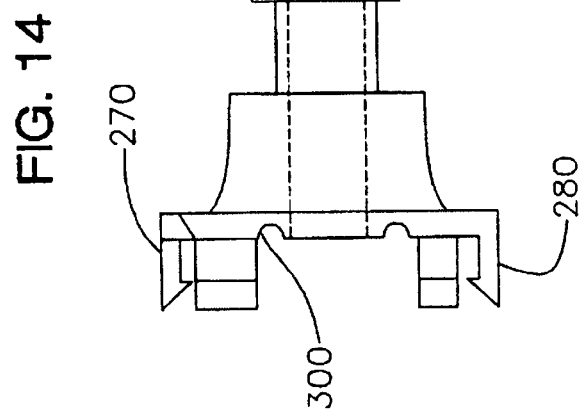
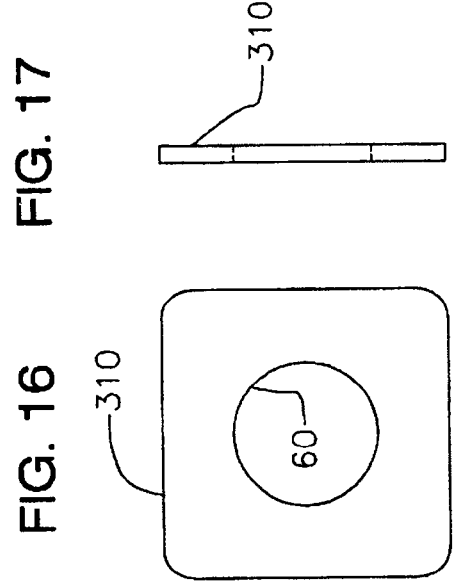
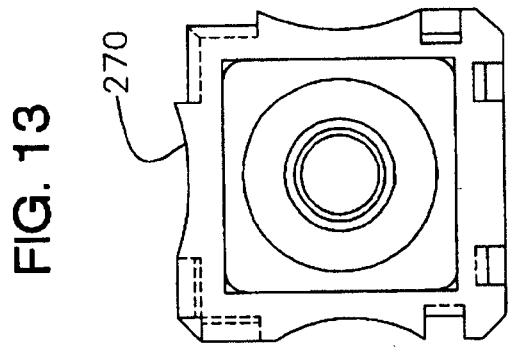

CONNECTION SYSTEM

BACKGROUND OF INVENTION

1. Field of Invention

The present invention relates generally to a method and apparatus to form sterile connections, and more particularly, a method and apparatus for inexpensively creating sterile connections in non-sterile environments.

2. Background of the Invention

Presently, the pharmaceutical industry is comprised of two manufacturing systems. The first manufacturing system is the traditional system that uses clean rooms, stainless steel reactors, holding tanks, and piping to maintain sterile conditions during manufacture. The second manufacturing system is state-of-the-art biotechnology manufacturing that uses an assortment of disposable plastic bags and flexible sterile tubing. With the traditional manufacturing methods, clean-in-place and steam-in-place systems are required to assure that the stainless steel reactors and piping remain clean and sterile. A sterile clean room is also required during traditional manufacturing processes so that when necessary connections are made that breach the sterile piping, the environment does not contaminate the fluid flow. Maintaining a clean room is time consuming and difficult to validate. In contrast, the state-of-the-art biotechnology methods use plastic bags and tubing sets that can be sterilized prior to implementation in the manufacturing process and are completely disposable. Biotechnology manufacturing methods require significantly less capital because no initial investment in expensive stainless steel reactors or piping is required.

The tubing in biotechnology manufacturing is used between process containers and equipment that require sterile connections. A sterile tube welding machine can be used to weld the thermoplastic tubing in a sterile manner without the need for a laminar flow cabinet or similar environmental control device. The tube welder sterilizes a cutting blade or wafer then moves the blade through the two ends of the tubing to be joined. Once both ends of the tubing have been cut, the machine aligns the ends of the tubes while maintaining a high temperature. After the thermoplastic tubes cool, a sterile weld is formed. Another system utilizes a self contained HEPA system and a sterile plastic connector to create the union; still using the heated blades.

The various types of sterile tubing welders have disadvantages in that there is a limited range of the size of tubing that can be welded by one particular tube welding machine. A tube welding machine is also usually limited in applicability to specific tube materials such as thermoplastic. Furthermore, tube welding machines are typically large, heavy, lack versatility, and expensive.

The biotechnology approach, out of necessity, requires large amounts of disposable flexible tubing. This tubing is used to convey the sterile contents of one bag to another. Each time a connection is made to add or remove contents of a bag, only one of four systems noted below can be used; each system has significant shortcomings.

TABLE 1

| Device | Cost per Connection | Comments |
|---|---|---|
| Terumo Sterile Connection Device | US $ 3.00 to 5.00 | Clean room required one-quarter inch O.D. maximum size; lab scale and R&D applications only. Requires thermoplastic elastomer (herein "TPE") for tube material. |
| Wave Reewelder | US $ 4.00 to 7.00 | Clean room required; tubing up to ¾" O.D. in size; requires TPE material; new and unproven design; expensive at US $ 35,000.00 per typical application. |
| CPT Aseptic Connection Device | US $ 7.00 to 10.00 | ½ by ¾ and ⅜ by ⅝ inch tubing; heavy and large; expensive at US $ 35,000.00 per typical application; uses only C-Flex TPE tubing. |
| Manual System | US $ 10.00 to 25.00 | Manual method requires clean room and clean hood utilizing sterile utensils and connections; training in sterile technique required. |

All of the systems listed above require the use of thermoplastic tubing (no silicone) except the manual system. The ideal aseptic/sterile connection system would have the following characteristics:

1. Applicability to a wide array of tubing materials and sizes;
2. Inexpensive to assemble and maintain;
3. Requires no capital equipment;
4. Operates without a clean room;
5. Disposable;
6. Reliable and repeatable; and
7. Operator independent.

The current systems in use presently fall short of meeting the ideal criteria. Thus, there is a need for a disposable aseptic connection system that does not require a tube welding machine. A disposable aseptic connection system that does not employ a tube welding machine could be used regardless of the tubing material, size or location, at a competitive cost. Additionally, once a company commits to this type of connector, all pre-sterile bags and tube sets can be supplied with the appropriate disposable aseptic connection system fittings already in place. Therefore, connections are simple, repeatable and validatable.

Prior art describes varying apparatus for accomplishing sterile connections using a disposable aespetic connection system. By way of example, U.S. Pat. No. 4,418,945 to Kellog describes sterile connectors having strips that are withdrawn to expose the ends of conduits attached to cooperating connectors. U.S. Pat. No. 4,149,534 to Tenczar describes sterile connectors for joining conduits having an adhesive release positioned on adjoining faces of the connectors. U.S. Pat. No. 4,030,494 to Tenczar describes sterile fluid connectors having cooperating heat penetratable and fusible plastic barriers for coupling two conduits. U.S. Pat. No. 4,022,205 to Tenczar describes sterile fluid connectors having cooperating adhesive surfaces that are jointly punctured upon coupling two conduits. U.S. Pat. No. 4,019,512 to Tenczar describes an adhesively sterile connector having a protective member that is progressively pulled away. U.S. Pat. No. 3,865,411 to Rowe et al. describes a sterile connector having an adhesive release and two connectors are used to make a connection. Rowe et al. teaches to align the adhesive portions; then the free ends of the adhesive are pulled thereby exposing the free ends of the connectors to form a sealed, sterile fluid passage.

Notwithstanding the existence of such prior art disposable aseptic connection systems, there is a need for an improved and more efficient apparatus and method for using a disposable aseptic connection system that can be used as either a temporary or permanent connection.

An objective of the present invention is to provide a disposable aseptic connection system that is a temporary and disposable connection.

Another objective of the present invention is to provide a disposable aseptic connection system that is adaptable to a permanent connection.

Another objective is to provide a connection that is reliable and repeatable.

Still another objective is to provide a disposable aseptic connection system that is operator independent.

Another objective is to provide a connection system that is applicable to a wide array of tubing materials and sizes.

Another objective is to provide a disposable aseptic connection system that is inexpensive to assemble and maintain and requires no expensive equipment.

Another objective is to provide an aseptic connection system that can operate without a clean room.

Another objective is to provide a connection means that is compatable with the standard sanitary fittings common to the biotechnology industry.

It is, therefore, to the effective resolution of the aforementioned problems and shortcomings of the prior art that the present invention is directed.

However, in view of the prior art at the time the present invention was made, it was not obvious to those of ordinary skill in the pertinent art how the identified needs could be fulfilled.

SUMMARY OF INVENTION

The present invention solves significant problems in the art by providing an apparatus for establishing an aseptic/sterile connection comprising a substantially flexible, substantially transparent sterile barrier enclosing a terminal end of a conduit, a resilient, deformable support card fixed to the sterile barrier having an outer face disposed about the terminal end of the conduit having an adhesive perimeter covered by a release paper, and a rolling membrane comprising a continuous, removable, yieldable, flexible strip material, a portion of which is removably adhered to the support card and overlies the end of the conduit, the rolling membrane having a free end whereby a force applied to the free end thereof withdraws the entire rolling membrane to expose the end of the conduit whereby an aseptic/sterile connection is achieved by adhering opposing support cards together, removing the rolling membrane thereby creating a sterile corridor between a first sterile barrier and a second sterile barrier, and mating the terminal end of a first conduit and a second conduit together.

Adhesive material is applied to the exposed side of the rolling membrane while the side of the rolling membrane abutting the sterile barrier enclosure is free of adhesive material and treated with a release coating. This is preferred so that no residue of adhesive could possibly contaminate a fluid path established through the sterile corridor.

A biocidal agent may be integrated into the adhesive perimeter and the rolling membrane to combat contamination by both fungi and bacteria. A variety of biocides may be utilized such as Intercide® ABF available from Akros Chemicals America in New Brunsick, N.J.

An important aspect of the invention is that each opposing connection is oriented in the proper fashion. The rolling membrane on each opposing connection must be correctly oriented or the membrane will be impossible to properly withdraw. If the opposing support cards are adhered in an incorrect orientation, a sterile connection cannot be made and the support cards must be pulled apart and discarded. To prevent incorrect orientation of the support cards, an embodiment of the present invention includes an orientation-specific latching means on the support card wherein two opposing support cards may only latch together in a single orientation. This is achieved by configuring each latch point in a predefined, geometric configuration. The orientation-specific latching means mechanically biases two opposing support cards together to provide a sterile connection.

In one embodiment of the invention, the novel connector is used with annular sanitary fittings. One and one half inch diameter sanitary fittings are standard in the biopharmaceutical manufacturing art. Polymer snap fittings are mechanical latches including one or more latching arms and corresponding latching notches. The latches in this embodiment snap together in an internal circumferential direction to form a genderless connector. The genderless connector provides the advantages of easy manipulation and reduced inventory requirements.

An internal circumferential direction defines a direction of the latches that snap together around the circumference of the inside of opposedly aligned fittings. The circumferential latches provide the proper orientation of one fitting relative to the other to ensure that the opposedly aligned rolling membranes achieve a sterile connection. Snap fittings are not capable of maintaining a sterile connection indefinitely due to the creep characteristics of the polymer. Therefore, a polymer snap fitting requires additional support to provide a permanent sterile connection. Prior art snap fittings include externally located latches so that the standard sanitary clamps cannot be used. However, the present embodiment of the novel invention provides low profile latches with internal circumferential orientation so that standard stainless steel clamps can be used in adapting the snap fitting connection to a permanent connection. Stainless steel sanitary clamps are readily available in the industry and can be used to adapt the novel temporary snap fitting connection to a permanent connection at the operator"s discretion. The stainless steel clamp encircles and permanently secures the snap fitting.

The properly aligned and oppositely aligned support cards that are coupled with the mechanical latching means results in the joining of both rolling membranes whereby adhesion of the rolling membranes is constrained to be simultaneous. Therefore, the sterile surface of one card to that of the opposing card is exposed concurrently forming a sterile connection.

The invention further comprises a resilient gasket surrounding the periphery of the terminal end of the conduit wherein opposing gaskets are mechanically biased against each other thereby forming a substantially fluid-tight connection between two conduits.

An advantage of the current invention is that the connection can be used as a temporary connection or adapted to a permanent connection with the use of a standard stainless steel clamp. Thus, two markets are served.

Another advantage of the present invention is the internal circumferential latching means that orientates one fitting to the other to assure alignment of one rolling membrane with the other. A radially directed latch would require a longer latch length and would then interfere with the clamp or require design modifications to the tapered section of the fitting around which the clamp rests. However, the present invention has the advantage that it can be used with standard sanitary fittings and the novel latching means can be manually activated or will be automatically engaged when the clamp is closed.

These and other important objects, advantages, and features of the invention will become clear as this description proceeds.

The invention accordingly comprises the features of construction, combination of elements, and arrangement of parts that will be exemplified in the description set forth hereinafter and the scope of the invention will be indicated in the claims.

BRIEF DESCRIPTION OF DRAWINGS

For a fuller understanding of the nature and objects of the invention, reference should be made to the following detailed description, taken in connection with the accompanying drawings, in which:

FIG. 4 is an elevated, front view of the card adhesive label and rolling membrane.

FIG. 5 is an elevated, rear view of the card adhesive label and rolling membrane.

FIG. 12 is an elevated, partially sectional side view of an embodiment of the invention using a genderless connector.

FIG. 13 is an elevated, partially sectional front view of the latching support card according to the invention.

FIG. 14 is an elevated, partially sectional side view of the latching support card according to the invention.

FIG. 15 is an elevated, partially sectional rear view of the latching support card according to the invention.

FIG. 16 is an elevated front view of the foam biasing pad according to the invention.

FIG. 17 is an elevated, partially sectional side view of the foam biasing pad according to the invention.

DETAILED DESCRIPTION

Figure 1:
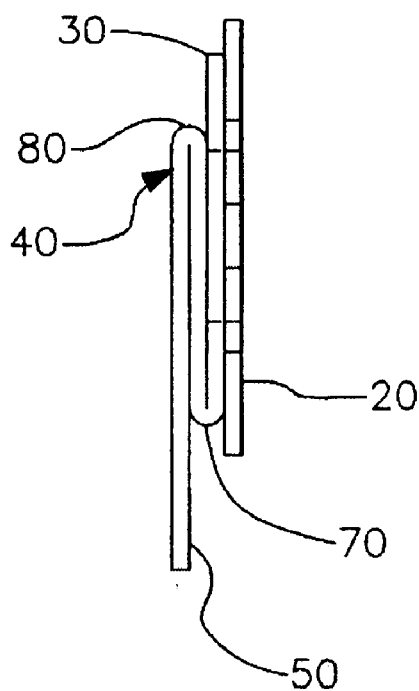
FIG. 1 is a side view of rolling membrane attached to the support card.
Figure 2:
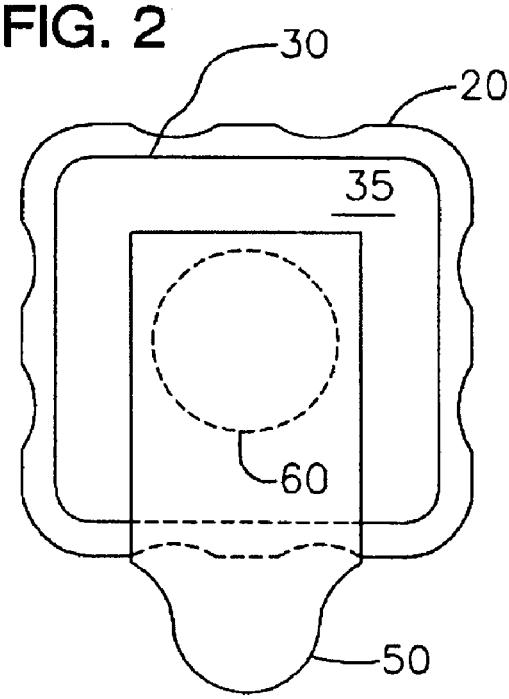
FIG. 2 is an elevated, partially sectional front view of the rolling membrane and support card.
Figure 3:
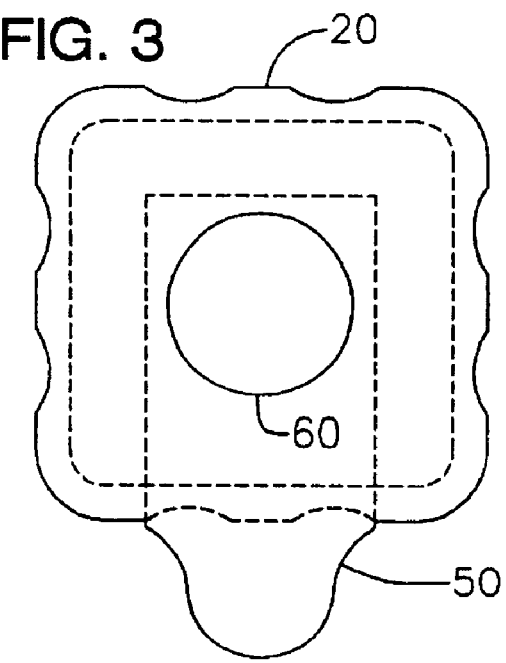
FIG. 3 is an elevated, partially sectional rear view of the rolling membrane and support card.

Referring initially to FIGS. 1–5, a support card 20 is provided which is substantially resilient and deformable. A card adhesive label 30 is provided having an adhesive front card label surface 130 forming a sterile safety zone and a non-adhesive rear card label surface 140. A conduit aperture 60 is provided through the support card 20 and the card adhesive label 30. A rolling membrane 40 is shown folded in FIGS. 1–3 and extended in FIGS. 4–5. The rolling membrane 40 has a first membrane fold 70, a second membrane fold 80 and a membrane pull grip 50. The area between the first membrane fold 70 and the second membrane fold 80 on the front of the card adhesive label 30 forms a front first fold release coating 90. This front first fold release coating 90 is in contact with the adhesive front card label surface 130. While in contact, the sterile safety zone is protected from contamination, even in a contaminated setting. The area between the second membrane fold 80 and the membrane pull grip 50 on the front of the card adhesive label 30 forms a front second fold adhesive coating. The area between the first membrane fold 70 and the second membrane fold 80 on the rear of the card adhesive label 30 forms a rear first fold release coating 100. The area between the second membrane fold 80 and the membrane pull grip 50 on the rear of the card adhesive label 30 forms a rear second fold release coating 110.

It can be seen in FIG. 1 that when the rolling membrane 40 is folded, the front first fold release coating 90 comes into contact with the front card label surface 130 thereby protecting the sterile safety zone. The rear first fold release coating 100 abuts the rear second fold release coating 110. The front second fold adhesive coating 120 is then exposed for adhesion to the adhesive coating 120 of an opposing rolling membrane. It can also be seen that the membrane pull grip 50 is disposed below the lower edge of the support card 20. Externally exposed adhesive surfaces, such as the front second fold adhesive coating 120, are covered by a release paper (not shown) that prevent drying of the adhesive material.

Figure 6:
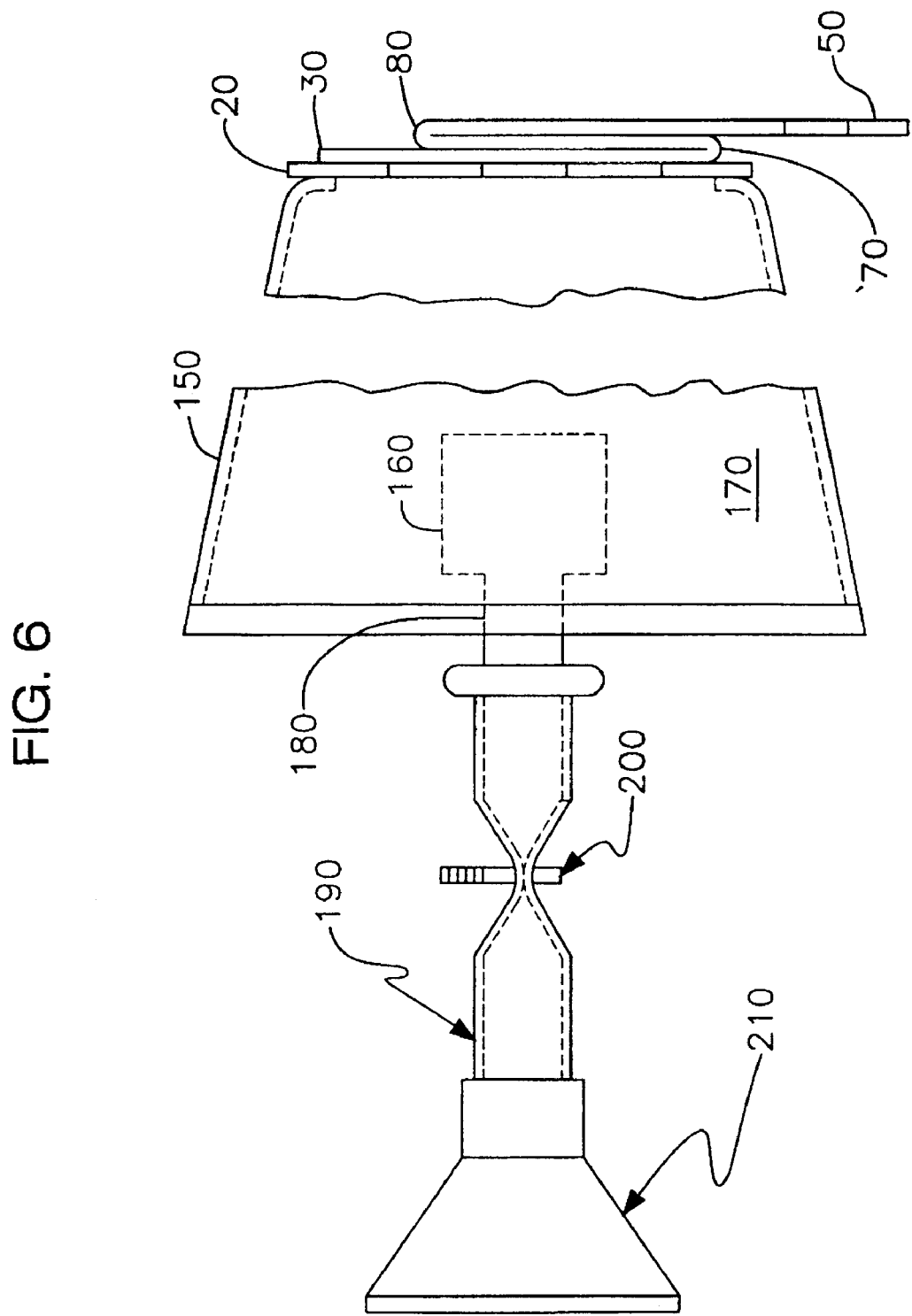
FIG. 6 is an elevated, partially sectional side view of the sterile barrier.

In FIG. 6, the support card 20 is fixed to one end of a sterile barrier 150 enclosing a conduit fitting 160. It is preferred that the sterile barrier 150 be constructed of a clear, flexible polymer material. Constructing the sterile barrier 150 out of substantially transparent material permits the user to easily view the manipulation of the conduits. The flexibility of the sterile barrier 150 enables the manipulation itself. The polymer material is preferred for its durability and its fluid containment qualities. Accordingly, the preferred sterile barrier 150 is flexible and movable. The conduit fitting 160 may be a male/female connector, a genderless connector, or the like. The sterile barrier 150 forms a sterile field 170 wherein the conduit fitting 160 and the interior of the sterile barrier 150 is aseptic/sterile. A barrier port 180 in the sterile barrier 150 provides an external fluid path from the conduit fitting 160 to an exterior tube 190. In this illustrative embodiment, a ladish fitting 210 mates with an external fluid path. A tubing clamp 200 is engaged by default thereby maintaining the sterility of the sterile field 170. However, the area from the tubing clamp 200 to the ladish fitting 210 is not sterile and therefore is sterilized once coupled to the fluid path. Once sterilized, both sides of the tubing clamp 200 are then aseptic/sterile and the tubing clamp 200 is disengaged. Well-known sterilization methods for this application typically include steam-in-place procedures.

Figure 7:
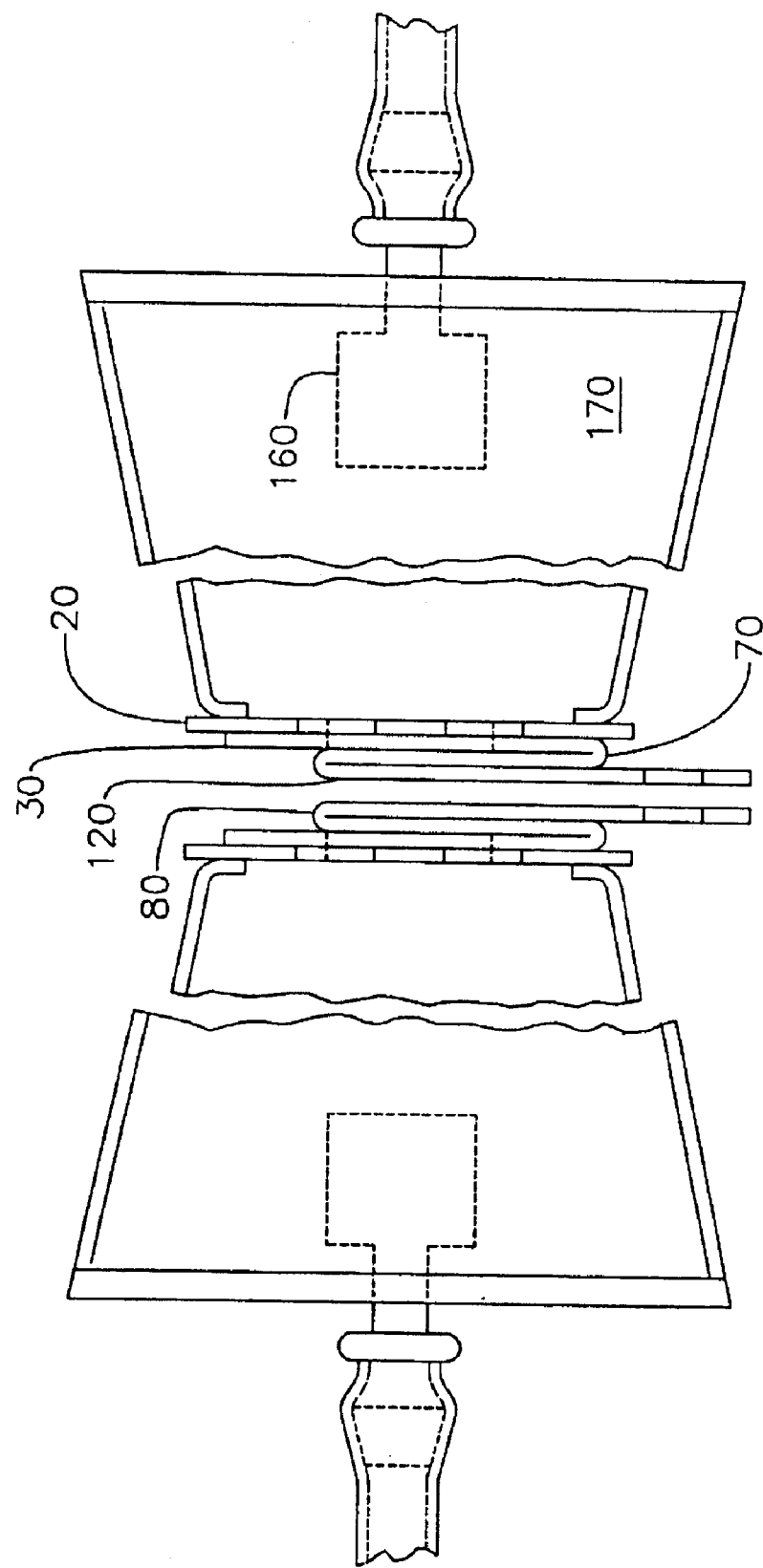
FIG. 7 is an elevated, partially sectional side view of two opposing rolling membranes aligned to mate two sterile barriers together.
Figure 8:
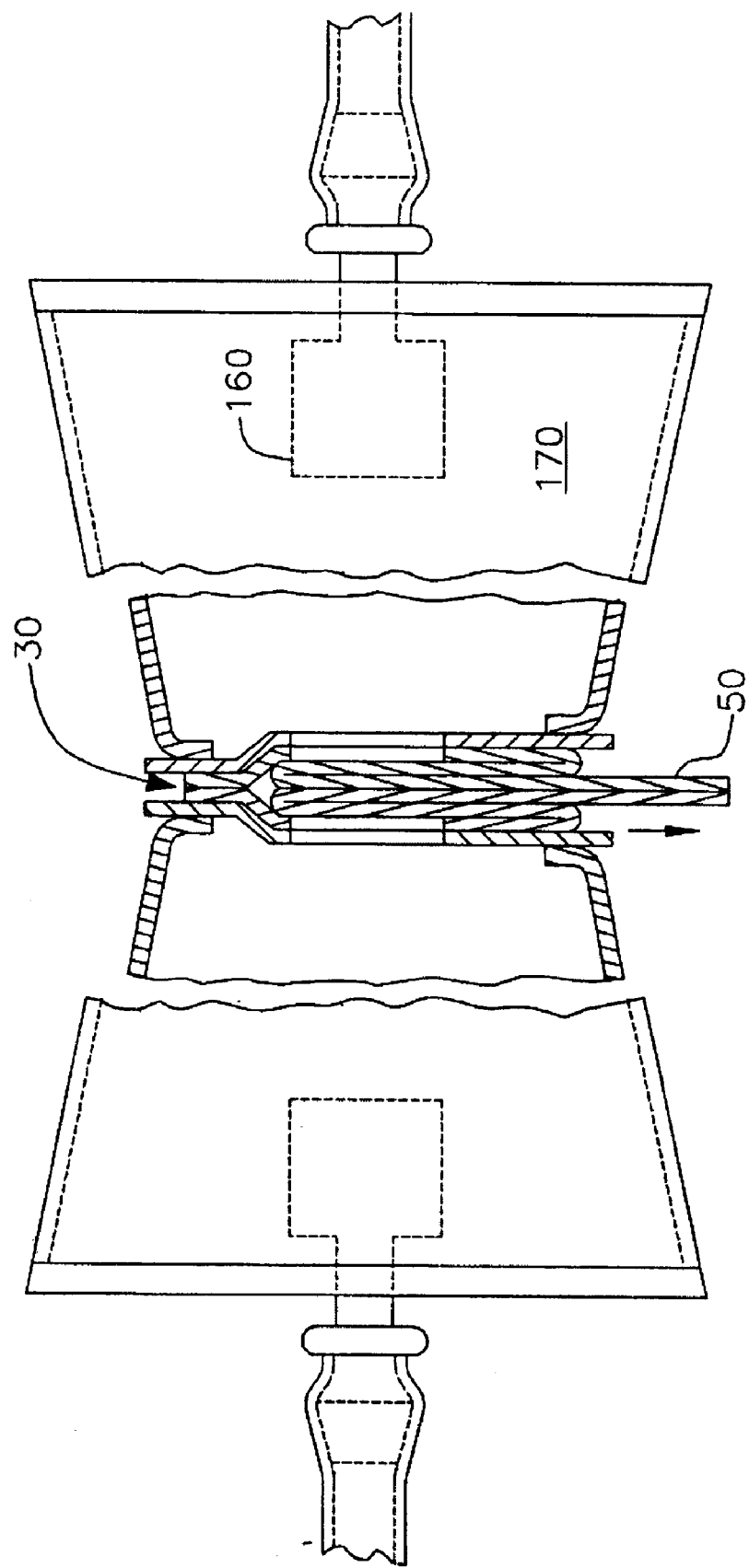
FIG. 8 is an elevated, partially sectional side view of two opposing rolling membranes and two opposing adhesive card perimeters adhered to each other.
Figure 9:
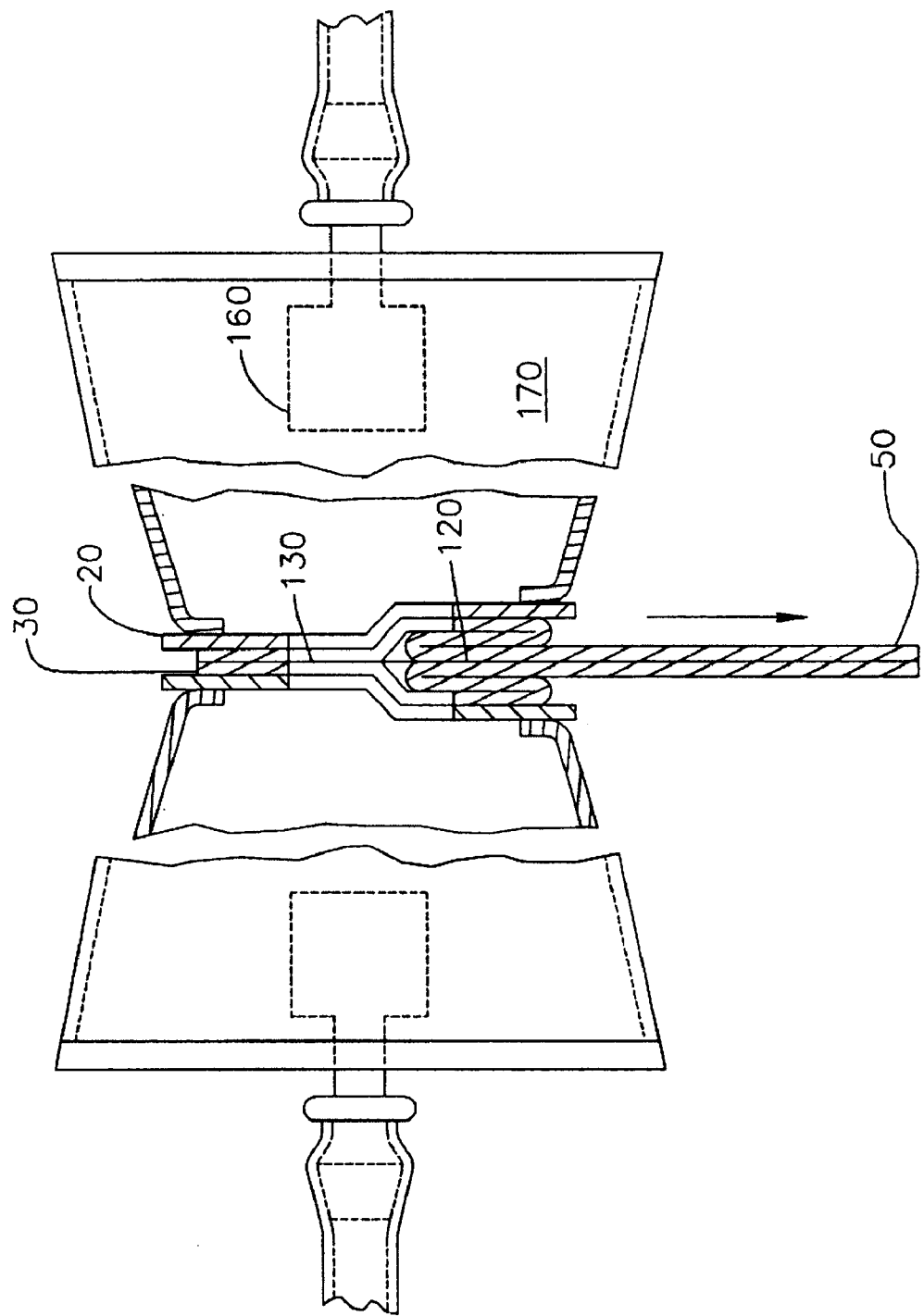
FIG. 9 is an elevated, partially sectional side view of the rolling membrane being withdrawn to open a sterile corridor between the two sterile barriers.
Figure 10:
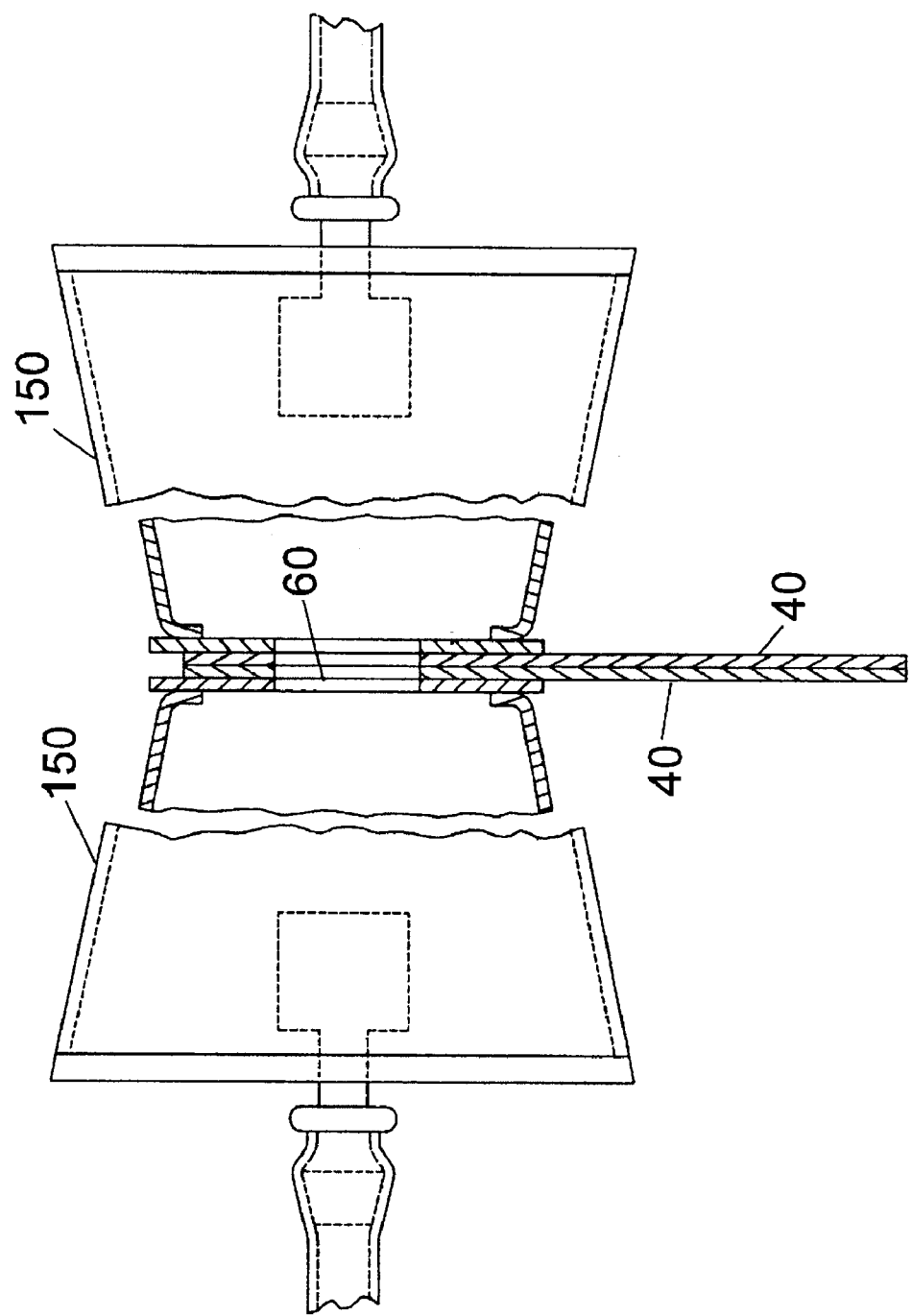
FIG. 10 is an elevated, partially sectional side view of the rolling membrane fully withdrawn between the two sterile barriers.
Figure 11:
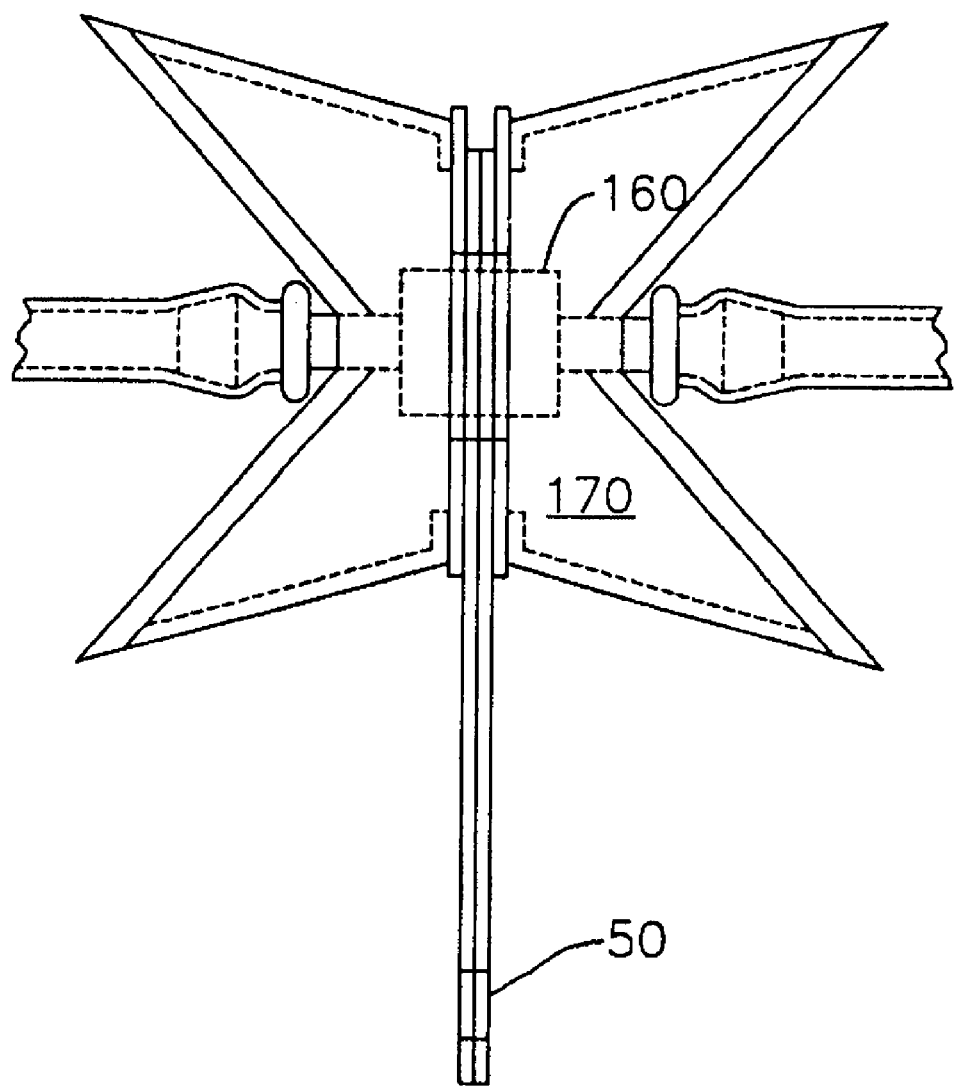
FIG. 11 is an elevated, partially sectional side view showing the mating of each conduit together within the sterile corridor formed between the two sterile barriers.
Figure 19:
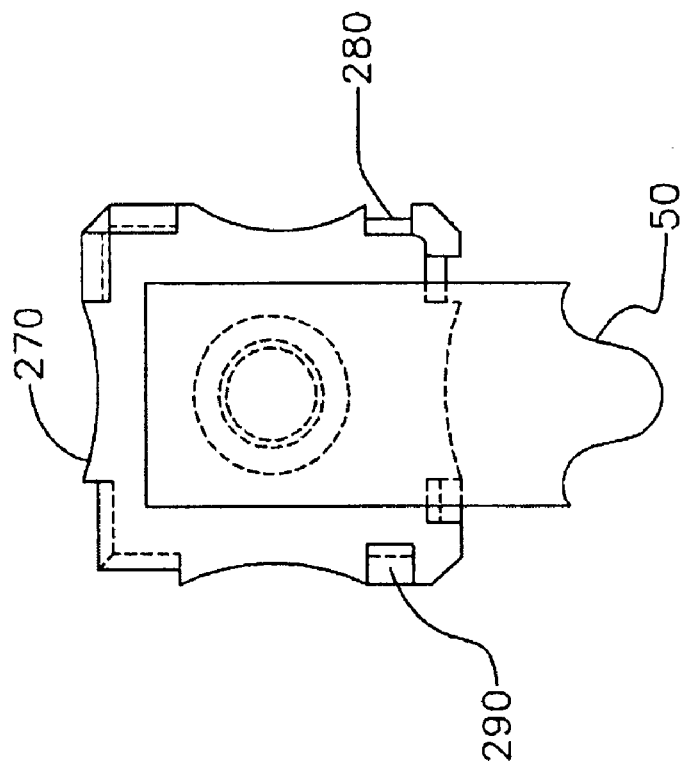
FIG. 19 is an elevated, partially sectional front view of an embodiment of the invention utilizing a latching card.

In FIG. 7, two opposing sterile barriers 150 are aligned so that the front second fold adhesive coating 120 of each rolling membrane 40 mirror each other. This alignment is important as the rolling membrane 40 may be withdrawn in only one linear direction. Once the two front second fold adhesive coating 120 surfaces are in contact, as shown in FIG. 8, the entire adhesive surface area of the front card label surface 130 also comes into contact thereby sealing each opposing support card 20 together. In FIG. 9, the membrane pull grip 50 is pulled away from the longitudinal axis of the sterile corridor thereby exposing the conduit aperture 60. With the front card label surface 130 already sealed, the sterile safety zone of each opposing card comes into contact with each other without exposure to the outside environment. In FIG. 10, the rolling membrane 40 is completely withdrawn to an unfolded configuration and the conduit apertures 60 are aligned to form a sterile corridor between each sterile barrier 150. In FIG. 11, each conduit fitting 160 is moved towards the conduit aperture 60, until both conduit fittings 160 mate with each other, thereby forming a secure fluid path. In a preferred embodiment, a genderless connector 250 is employed for the conduit fitting 160 as shown in FIG. 12. The genderless connector 250 provides the advantages of easy manipulation and reduced inventory requirements.

Figure 18:
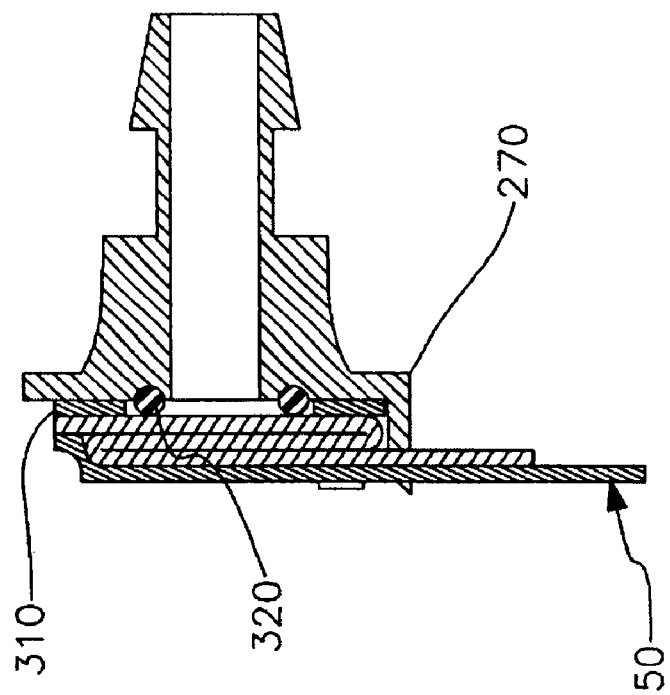
FIG. 18 is an elevated, partially sectional side view of an embodiment of the invention utilizing a latching card.

As indicated previously, the rolling membrane 40 must be withdrawn in a singular linear direction. Accordingly proper orientation of each opposing support card 20 is critical. The invention further comprises a third embodiment which abrogates the need for a flexible, transparent barrier. In the third embodiment, a mechanical latching means biases two opposing conduits together in strict orientation. While the user is unable to view the actual mating of the two or more conduits, the mechanical latching embodiment may provide a simple and efficiently manufactured connection system for the appropriate application. In FIGS. 13–15, a latching support card 270 is provided having at least one or more latching arms 280 and corresponding latching notches 290 arranged in a predetermined configuration to permit latching in only one orientation. The latching support card 270 may serve an additional purpose of providing mechanical force to bias two conduit ends to form a fluid path without additional fittings. In an illustrative embodiment, the latching support card 270 of FIG. 14 has a gasket channel configured to receive a gasket 320 of FIG. 18. A substantially resilient foam biasing pad 310 shown in FIGS. 16–18 pushes opposing latching support cards 270 away from each other as they are engaged by said latching arms 280. The compression force generated by the latching mechanisms seals each opposing gasket 320 against each other thereby forming a fluid path between the two conduits.

Figure 20:
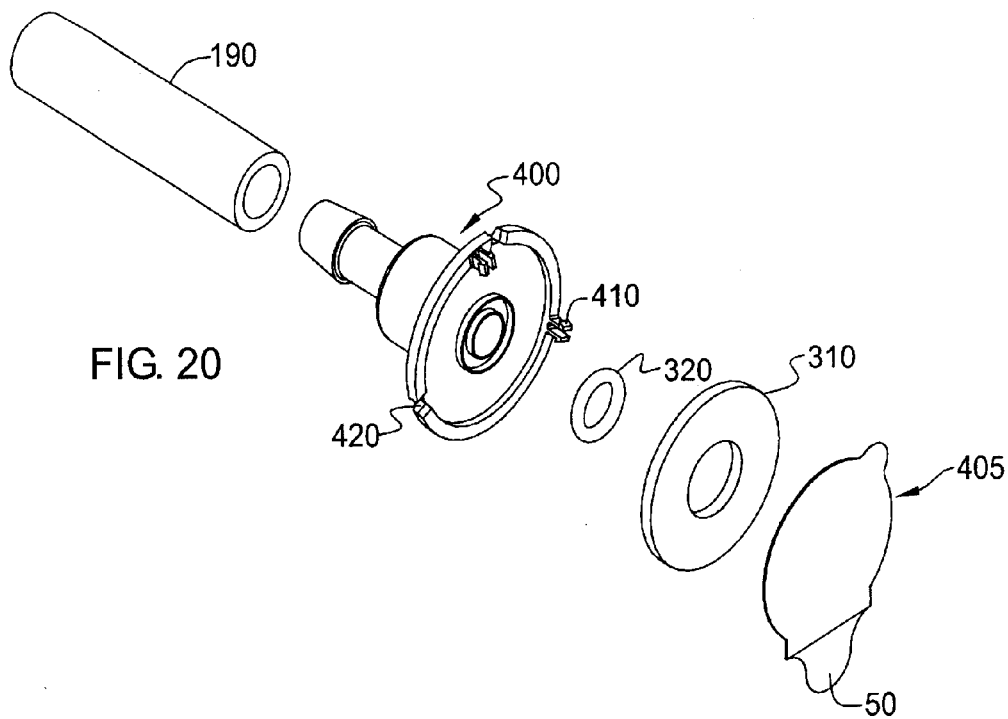
FIG. 20 is an exploded, perspective view of an embodiment of the invention utilizing sanitary fittings with internally circumferential orientated latches.
Figure 21:
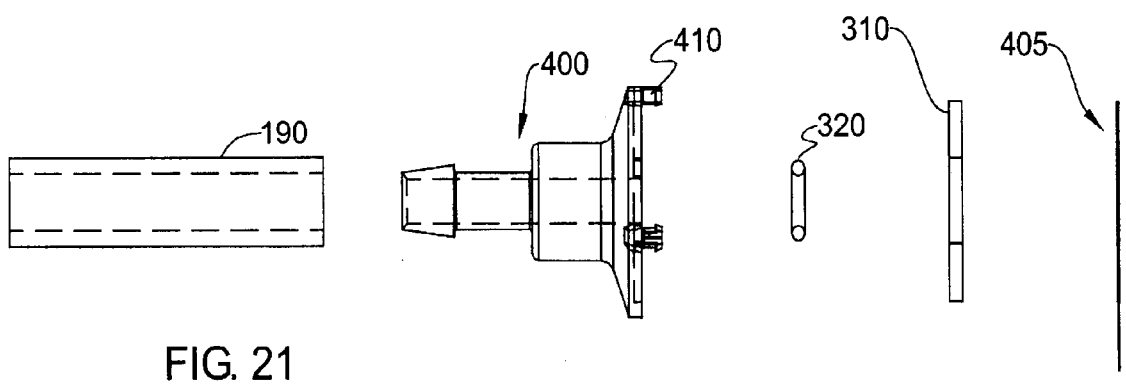
FIG. 21 is an exploded side view of an embodiment of the invention utilizing sanitary fittings with internally circumferential orientated latches.
Figure 22:
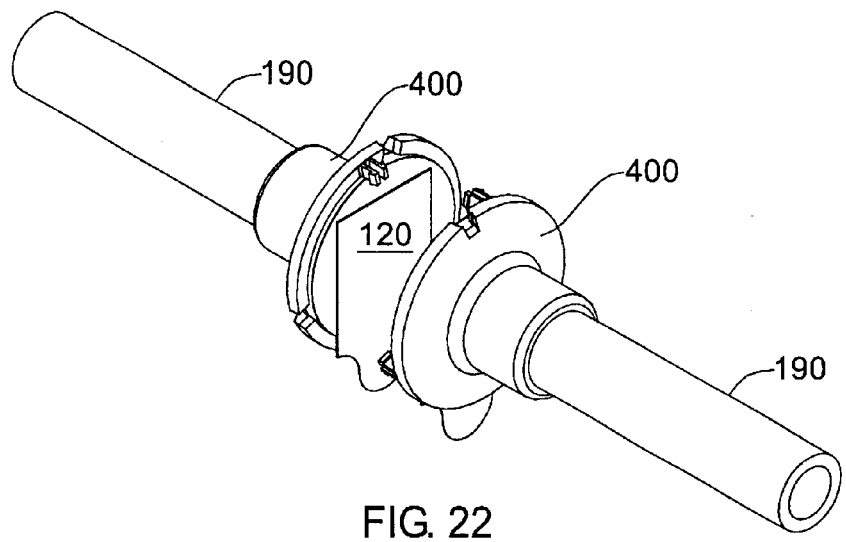
FIG. 22 is a perspective view of a pair of connectors of the present invention aligned to be assembled.
Figure 23:
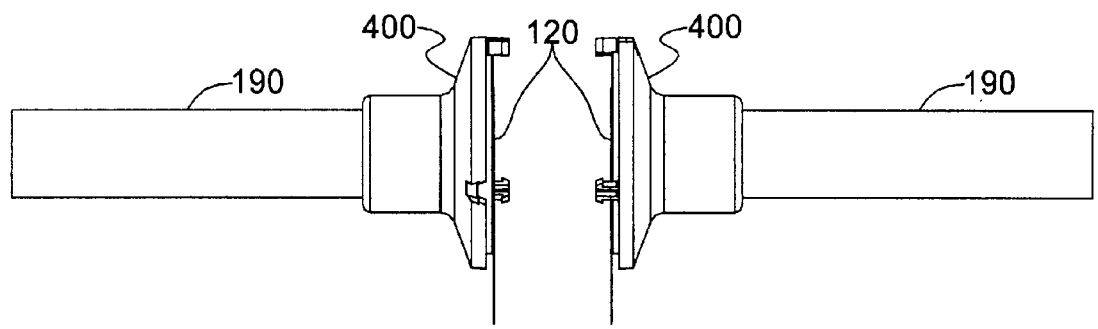
FIG. 23 is an elevated side view of a pair of connectors of the present invention aligned to be assembled.
Figure 24:
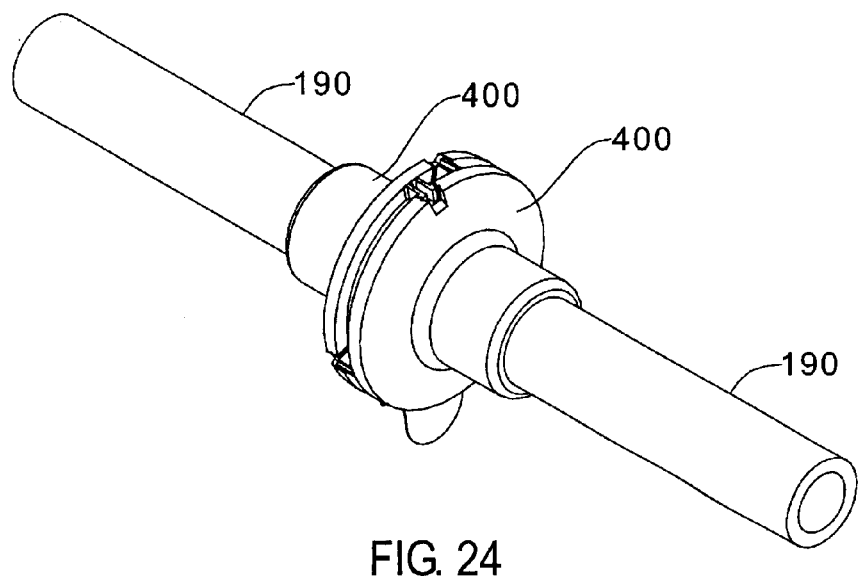
FIG. 24 is a perspective view showing the connectors fully assembled.
Figure 25:
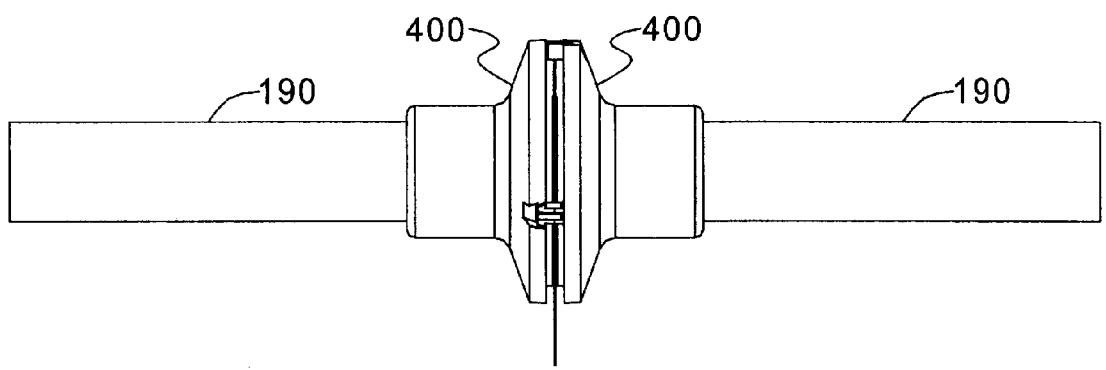
FIG. 25 is an elevated side view of the connectors fully assembled.
Figure 26:
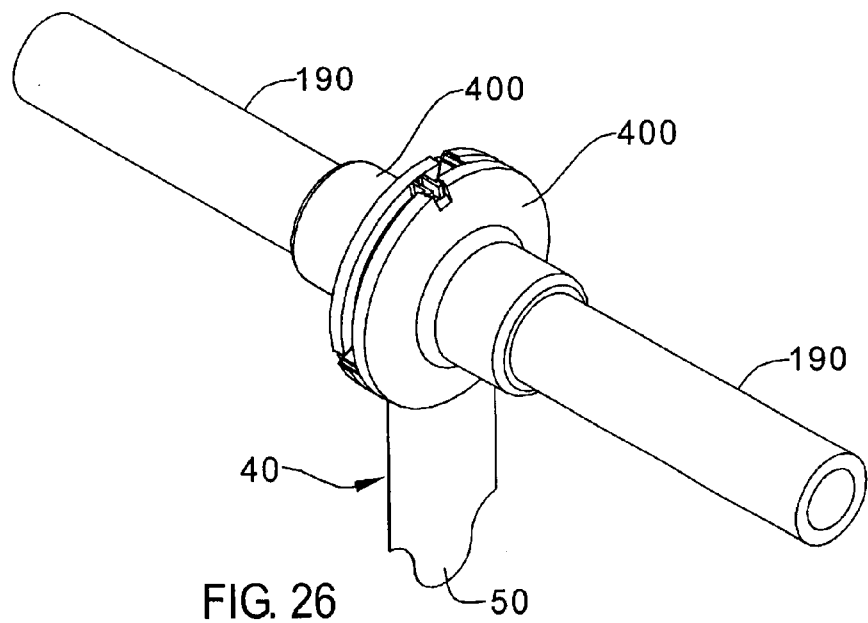
FIG. 26 is a perspective view of the rolling membrane being withdrawn to open a sterile corridor between the two sanitary fittings.
Figure 27:
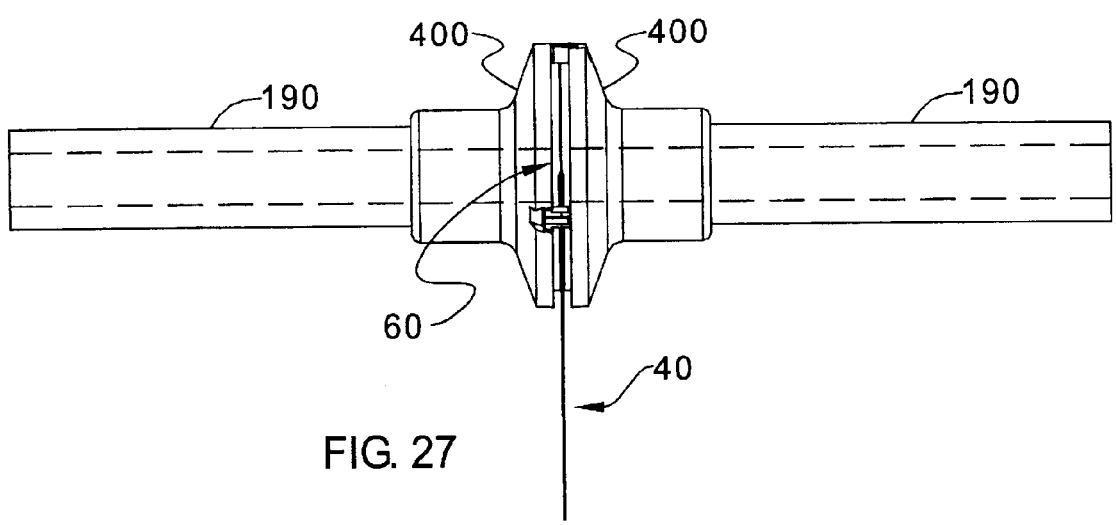
FIG. 27 is an elevated side view of the rolling membrane being withdrawn to open a sterile corridor between the two sanitary fittings.
Figure 28:
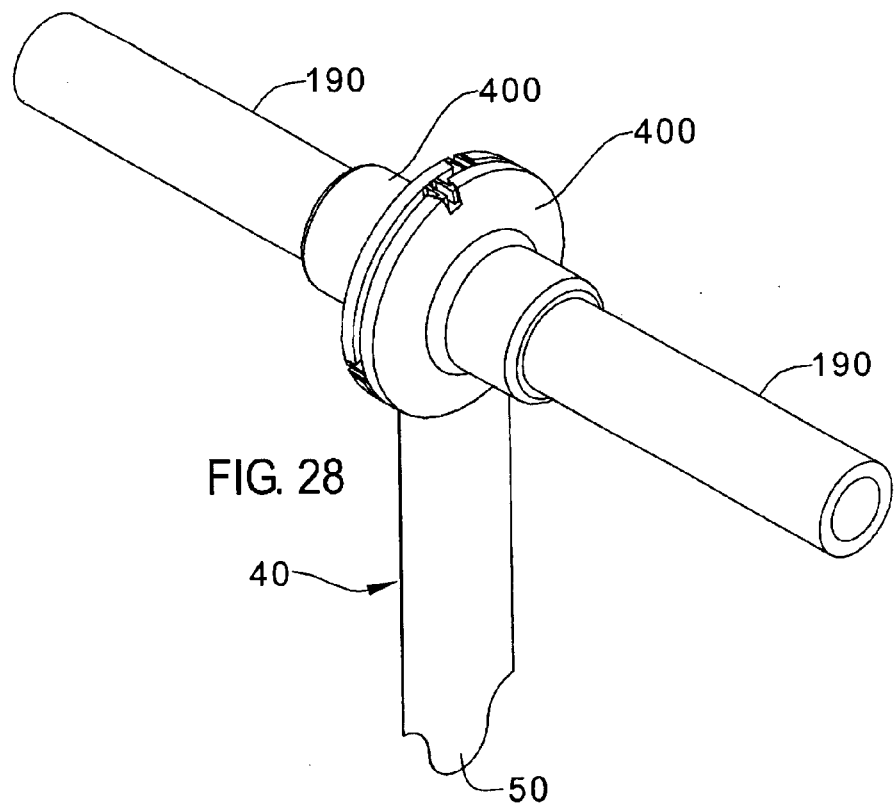
FIG. 28 is a perspective view of the rolling membrane being withdrawn to open a sterile corridor between the two sanitary fittings.
Figure 29:
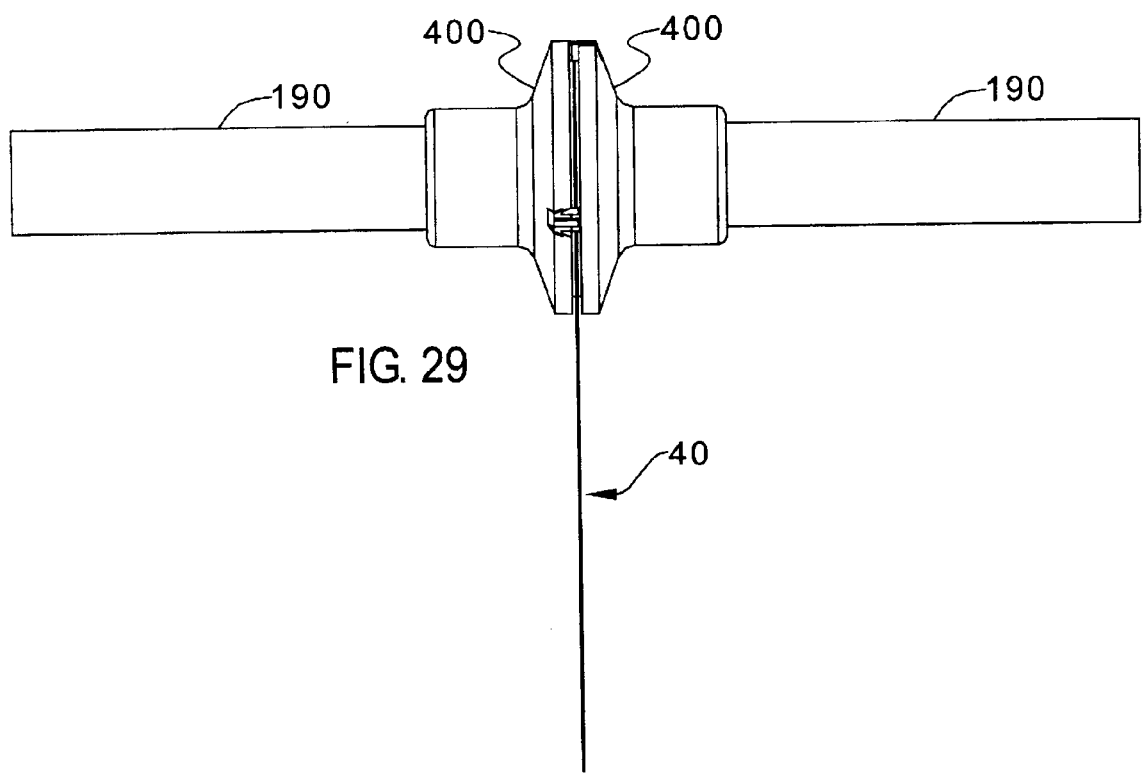
FIG. 29 is an elevated side view of the rolling membrane being withdrawn to open a sterile corridor between the two sanitary fittings.
Figure 30:
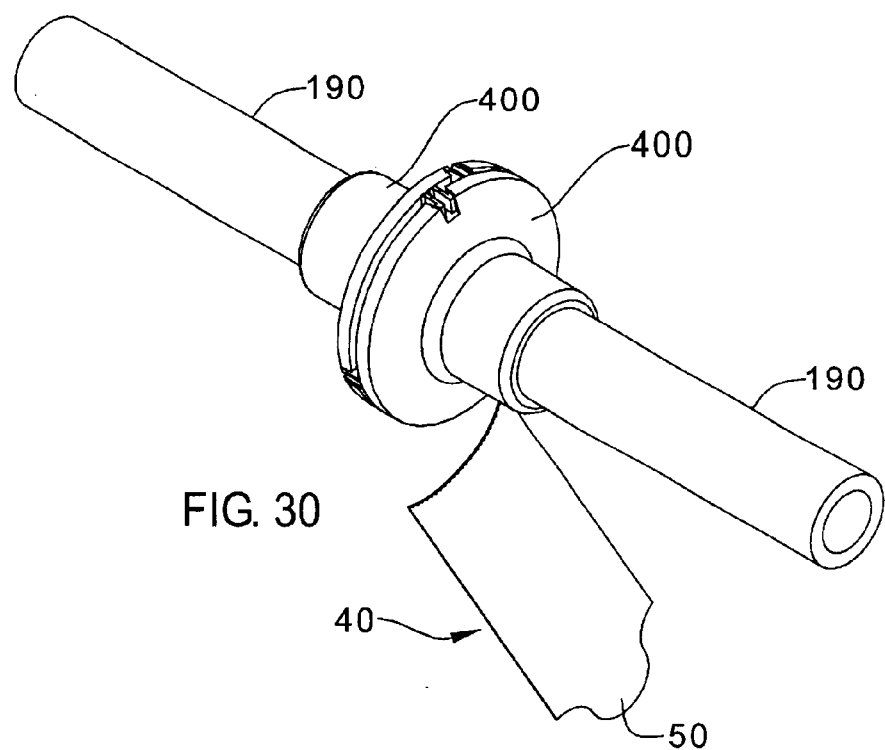
FIG. 30 is a perspective view of the rolling membrane fully withdrawn between the two sanitary fittings.
Figure 31:
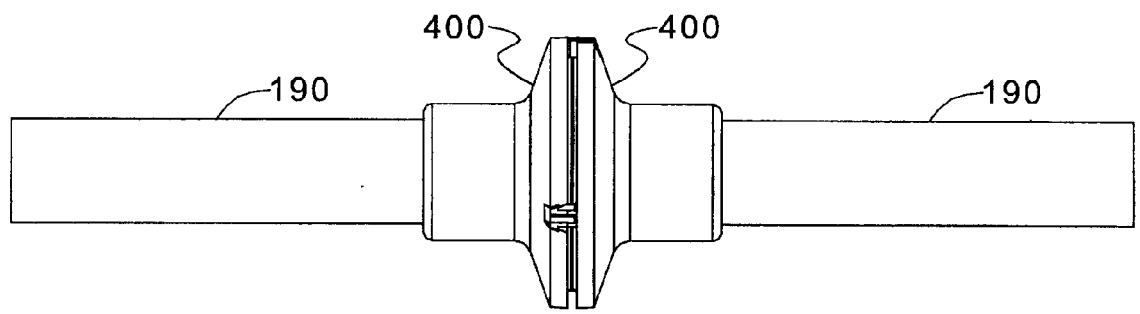
FIG. 31 is an elevated side view of the rolling membrane fully withdrawn to open a sterile corridor between the two sanitary fittings.

In an alternative embodiment, the novel connector is used with annular sanitary fittings 400. FIGS. 20 and 21 show the polymer sanitary snap fittings with novel mechanical latches including one or more latching arms 410 and corresponding latching notches 420 arranged in an internal circumferential manner on the sanitary fitting 400. The internal circumferential latches provide the proper orientation of one fitting 400 relative to the other to ensure that the opposedly aligned adhesive labels 405 attached to the sanitary fitting 400 achieve a sterile fluid connection. In FIGS. 22 and 23, two adhesive labels 405 are aligned so that the front second fold adhesive coating 120 of each adhesive label 405 mirror each other. This alignment is important as the rolling membrane 40 may be withdrawn in only one linear direction. Once the two front second fold adhesive coating 120 surfaces are in contact, as shown in FIGS. 24 and 25, the entire adhesive surface area of the front card label surface 130 also comes into contact thereby sealing each sanitary fitting 400 together. In FIGS. 26–29, the membrane pull grip 50 is pulled away from the longitudinal axis of the sterile conduit 190 thereby exposing the conduit aperture 60. With the front card label surface 130 already sealed, the sterile safety zone of each opposing sanitary fitting 400 comes into contact with each other without exposure to the outside environment. In FIGS. 30 and 31, the rolling membrane 40 is completely withdrawn to an unfolded configuration and the conduit apertures 60 are aligned to form a sterile corridor. The rolling membrane 40 is then removed by tearing away at fold 70.

Figure 32:
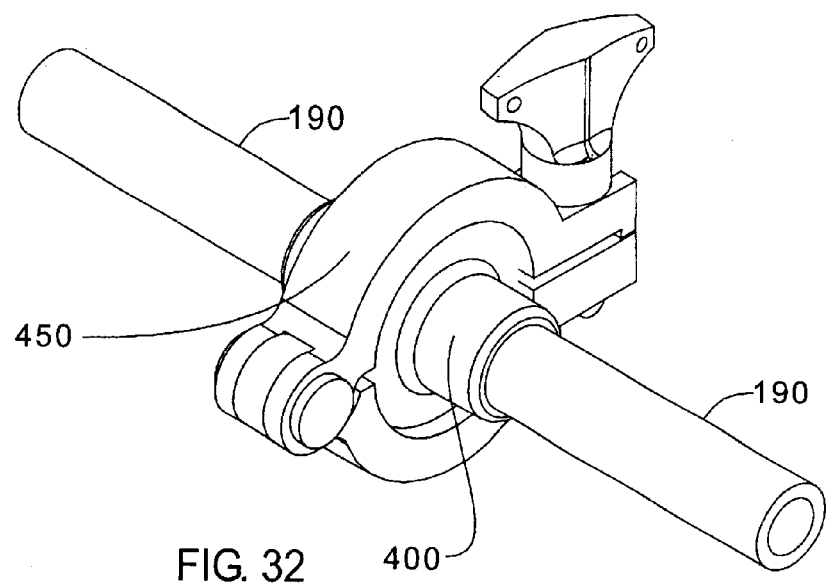
FIG. 32 is a perspective view of the stainless steel clamp engaged with the sanitary fittings.
Figure 33:
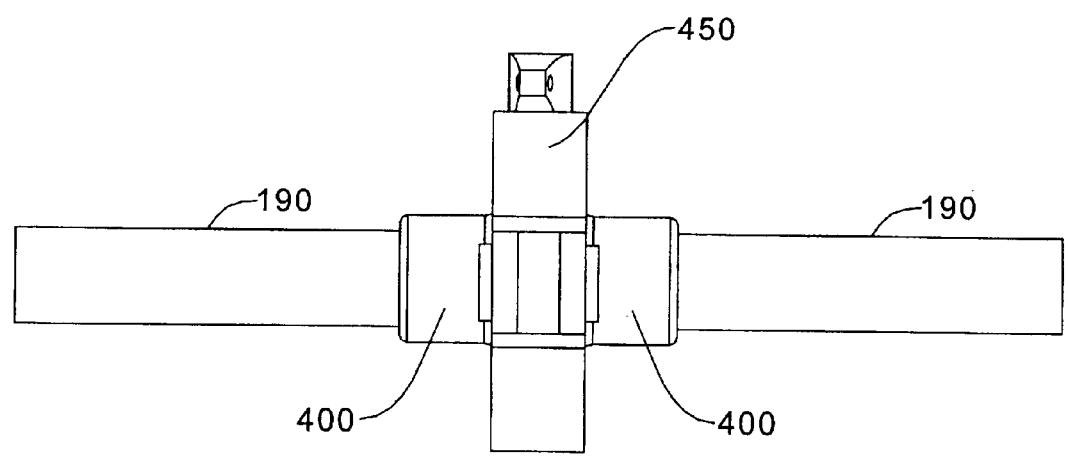
FIG. 33 is an elevated view of the stainless steel clamp engaged with the sanitary fittings.
Figure 34:
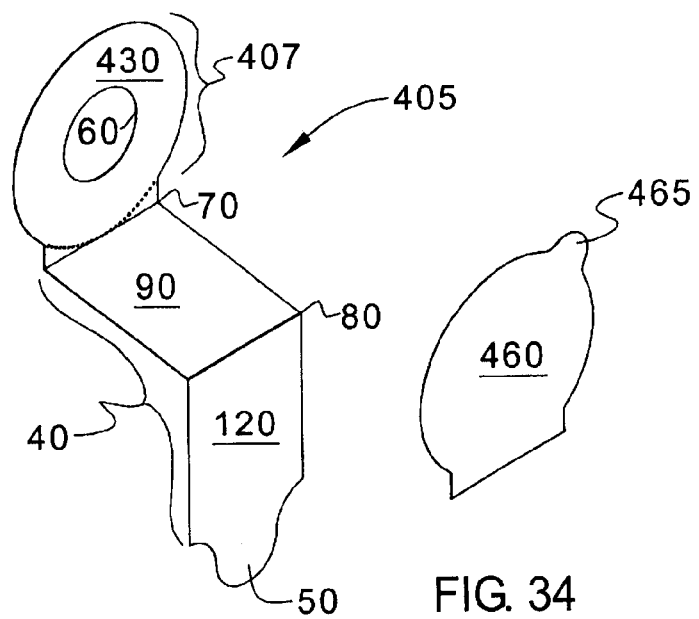
FIG. 34 is a perspective view of the annular adhesive label in a partially folded orientation.
Figure 35:
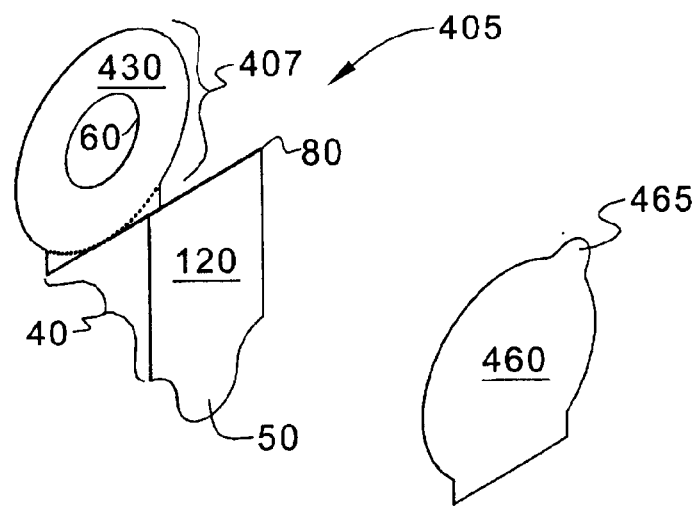
FIG. 35 is a perspective view of the annular adhesive label in a further partially folded orientation.
Figure 36:
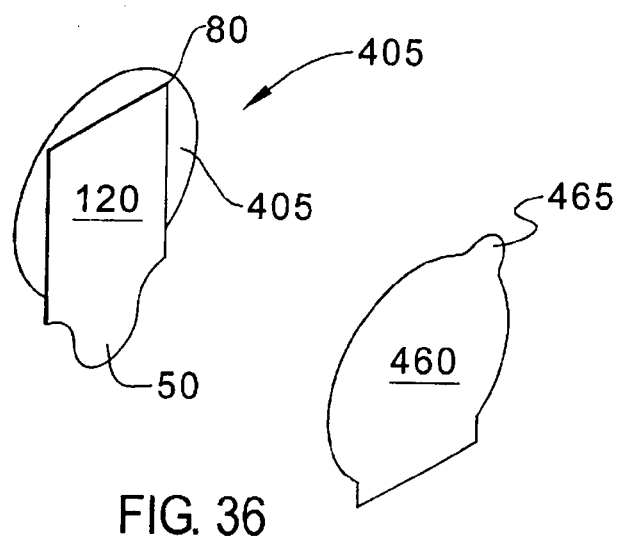
FIG. 36 is a perspective view of the annular adhesive label in a fully folded orientation.
Figure 37:
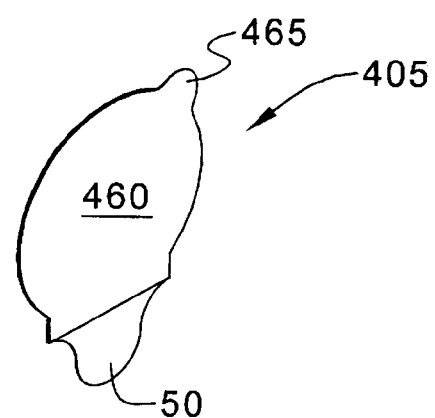
FIG. 37 is a perspective view of the annular adhesive label in a fully folder position and covered with release paper.

Complementary stainless steel sanitary clamps 450 shown in FIGS. 32 and 33 can be used with the sanitary fitting 400 to adapt a temporary snap fitting to a permanent connection. Thus, this embodiment of the novel invention provides a low profile latch, one that will not interfere with the clamp in adapting the snap fitting to a permanent connection and is heretofore unknown in the art.

FIGS. 34–37 show the steps of folding rolling membrane 40 into a ready position onto annular support card 407 and covered by release paper 460. The removable release paper 460 is provided with a pull tab 465 so that the release paper can be easily removed from adhesive face 120 when connecting two sanitary fittings 400.

It will be seen that the objects set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described.

What is claimed is:

1. An apparatus for establishing an aseptic/sterile connection comprising:
   a substantially flexible, substantially transparent sterile barrier enclosing a terminal end of a conduit; a resilient, deformable support card fixed to said sterile barrier having an outer face disposed about said terminal end of said conduit having an adhesive perimeter covered by a release paper; and a rolling membrane comprising a continuous, removable, yieldable, flexible strip material, a portion of which is removably adhered to said support card and overlies the end of said conduit forming a sterile safety zone, said rolling membrane having a free end; whereby a force applied to the free end thereof withdraws the entire rolling membrane to expose the end of said conduit whereby an aseptic/sterile connection is achieved by adhering opposing support cards together, removing said rolling membrane thereby creating a sterile corridor between a first sterile barrier and a second sterile barrier, and mating the terminal end of a first conduit and a second conduit together.

2. The apparatus of claim 1 wherein said adhesive perimeter includes a biocidal agent.

3. The apparatus of claim 1 wherein said rolling membrane includes a biocidal agent.

4. The apparatus of claim 1 further comprising an orientation-specific latching means on said support card wherein two opposing support cards may only latch together in a single orientation.

5. The apparatus of claim 4 wherein said orientation-specific latching means mechanically biases two opposing support cards together.

6. The apparatus of claim 5 further comprising a resilient gasket surrounding the periphery of said terminal end of said conduit wherein opposing gaskets are mechanically biased against each other thereby forming a substantially fluid-tight connection between two conduits.

7. The apparatus of claim 1 further comprising a genderless connector mated to said terminal end of said conduit.

8. An apparatus for establishing an aseptic/sterile connection comprising:
   an orientation-specific latching means enclosing a terminal end of a conduit wherein two opposing latching means may only latch together in a single orientation; a rigid latching support card having an outer face disposed about said terminal end of said conduit having an adhesive perimeter covered by a release paper; a resilient annular gasket surrounding the periphery of said terminal end of said conduit and a resilient foam biasing pad surrounding said resilient annular gasket wherein opposing resilient annular gaskets and resilient foam biasing pads are mechanically biased against each other thereby forming a substantially fluid-tight connection between two conduits; and a rolling membrane comprising a continuous, removable, yieldable, flexible strip material, a portion of which is removably adhered to said rigid latching support card and overlies the end of said conduit forming a sterile safety zone, said rolling membrane having a free end; whereby a force applied to the free end thereof withdraws the entire rolling membrane to expose the end of said conduit whereby an aseptic/sterile connection is achieved by latching opposing rigid latching support cards together, removing said rolling membrane thereby creating a sterile corridor, and mating the terminal end of a first conduit and a second conduit together.

9. The apparatus of claim 8 wherein said adhesive perimeter includes a biocidal agent.

10. The apparatus of claim 8 wherein said rolling membrane includes a biocidal agent.

11. The apparatus of claim 8 further comprising a genderless connector mated to said terminal end of said conduit.

12. An apparatus for establishing an aseptic/sterile connection comprising:
    an internal circumferential latching means enclosing respective terminal ends of two longitudinally aligned conduits wherein two opposing latching means may only latch together in a single orientation; each opposing latching means provided in the form of a sanitary fitting having a rear part that engages a terminal end of an associated conduit and having an annular front surface having a diameter greater than its associated conduit: each front surface of said opposing sanitary fittings being centrally apertured; a first annular ridge disposed in surrounding relation to each of said central apertures; a second annular ridge disposed in surrounding relation to each of said first annular ridges; an annular gasket snugly positioned on each of said opposing front surfaces between said first and second annular ridges; a third annular ridge formed on a peripheral edge of each of said front surfaces; a toroidal foam biasing pad snugly positioned on each of said front surfaces between said second and third annular ridges; and a pair of rolling membranes, each of which includes a continuous, removable, yieldable, flexible strip material, an adhesive label portion of which is removably adhered to an associated annular gasket and toroidal foam biasing pad and overlies the terminal end of its associated conduit forming a sterile safety zone, each of said rolling membranes having a free end; whereby a force applied to said respective free ends thereof withdraws the entire rolling membrane to expose the terminal end of said associated conduit whereby an aseptic/sterile connection is achieved by latching opposing latching means together, adhering opposing adhesive labels together, removing said rolling membranes thereby creating a sterile corridor, and mating the terminal end of said conduits together.

13. The apparatus of claim 12 wherein said adhesive perimeter includes a biocidal agent.

14. The apparatus of claim 12 wherein said rolling membrane includes a biocidal agent.

15. The apparatus of claim 12 wherein said orientation-specific latching means mechanically biases said annular gaskets and toroidal foam biasing pads together.

16. An apparatus for establishing an aseptic/sterile connection between respective terminal ends of a first and a second conduit where said first and second conduits have a common internal diameter and are positioned along a common longitudinal axis of symmetry, comprising:

a first support card having a deformable, resilient construction;

said first support card having a front surface and a rear surface;

a first support card central aperture formed in said first support card;

a first adhesive label disposed in overlying relation to said front surface of said first support card;

a first adhesive label central aperture formed in said first adhesive label;

said rear surface of said first support card being adhesive-free and said rear surface adapted to abut a terminal end of said first conduit;

said first support card central aperture and said first adhesive label central aperture sharing a common predetermined diameter equal to said inner diameter of said first conduit;

said first support card central aperture and said first adhesive label central aperture having their respective centers coincident with said common longitudinal axis of symmetry;

a first rolling membrane formed integrally with said first adhesive label;

a first fold being formed in said first rolling membrane to form a first section, said first section having a rear surface disposed in overlying relation to said first adhesive label and being releasably adhered thereto, said first section having a width greater than the common diameter of said respective central apertures formed in said first support card and said first adhesive label;

a second fold being formed in said first rolling membrane to form a second section, said second section having a rear surface disposed in overlying relation to said first section and being releasably adhered thereto;

an adhesive applied to a front surface of said first rolling membrane second section;

a first pull grip formed integrally with said first rolling membrane second section, said first pull grip having front and rear surfaces that are adhesive-free;

a second support card having a deformable, resilient construction;

said second support card having a front surface and a rear surface;

a second support card central aperture formed in said second support card;

a second adhesive label disposed in overlying relation to said front surface of said second support card;

a second adhesive label central aperture formed in said second adhesive label;

said rear surface of said second support card being adhesive-free and said rear surface adapted to abut a terminal end of said second conduit;

said second support card central aperture and said second adhesive label central aperture sharing a common predetermined diameter equal to said inner diameter of said second conduit;

said second support card central aperture and said second adhesive label central aperture having their respective centers coincident with said common longitudinal axis of symmetry;

a second rolling membrane formed integrally with said second adhesive label;

a first fold being formed in said second rolling membrane to form a first section, said second rolling membrane first section having a rear surface disposed in overlying relation to said second adhesive label and being releasably adhered thereto, said second rolling membrane first section having a width greater than the common diameter of said respective central apertures formed in said second support card and said second adhesive label;

a second fold formed in said second rolling membrane to form a second section, said second rolling membrane second section having a rear surface disposed in overlying relation to said second rolling membrane first section and being releasably adhered thereto;

an adhesive applied to a front surface of said second rolling membrane second section;

a second pull grip formed integrally with said second rolling membrane second section, said second pull grip having front and rear surfaces that are adhesive-free;

said first rolling membrane and said second rolling membrane being disposed in sandwiched relation between said first and second support cards and said first and second support cards being disposed, under compression, in sandwiched relation between said respective terminal ends of said first and second conduits;

whereby said front surface of said first rolling membrane second section and said front surface of said second rolling membrane second section are disposed in abutting relation to one another, in sandwiched relation between said first and second support cards, when said terminal end of said first conduit is disposed in abutting relation to said rear surface of said first support card and said terminal end of said second conduit is disposed in abutting relation to said rear surface of said second support card;

whereby pulling said first and second pull grips in a radial direction away from said common longitudinal axis of said first and second conduits removes said first and second rolling membranes from their sandwiched position between said first and second adhesive labels so that said first and second adhesive labels are urged into abutting relation to one another by the inherent resiliency of said first and second support cards and adhere to one another to thereby join together said first and second support cards and said respective terminal ends of said first and second conduits.

17. The apparatus of claim 16, further comprising:

a biocidal agent applied to said first and second support cards.

18. The apparatus of claim 16, further comprising:

a biocidal agent applied to said first and second rolling membranes.

19. The apparatus of claim 16, further comprising:

a first conduit fitting secured to said terminal end of said first conduit;

a second conduit fitting secured to said terminal end of said second conduit;

a first sterile barrier that houses said terminal end of said first conduit and said first conduit fitting;

a second sterile barrier that houses said terminal end of said second conduit and said second conduit fitting;

said first sterile barrier having an open end closed by said first support card; and said second sterile barrier having an open end closed by said second support card;

whereby respective interiors of said first and second sterile barriers are maintained in a sterile condition.

20. The apparatus of claim 19, further comprising:
a first genderless connector secured to said terminal end of said first conduit; and
a second genderless connector secured to said terminal end of said second conduit;
whereby said first and second genderless connectors facilitate interconnection of said respective terminal ends of said first and second conduits.

21. An apparatus for establishing an aseptic/sterile connection between respective terminal ends of a first and a second conduit where said first and second conduits have a common internal diameter and are positioned along a common longitudinal axis of symmetry, comprising:
a first rigid latching support card;
said first rigid latching support card having a rear surface adapted to engage a terminal end of a first conduit;
said first rigid latching support card having a front surface having a diameter greater than a diameter of said first conduit;
said first rigid latching support card having a central bore formed therein that is in fluid communication with said terminal end of said first conduit;
said front surface of said first rigid latching support card being centrally apertured, said central aperture being the forward extent of said central bore;
a first annular gasket of resilient construction positioned on said front surface of said first rigid latching support card in surrounding relation to said central aperture formed in said front surface;
a first resilient foam biasing pad disposed on said front surface of said first rigid latching support card in surrounding relation to said first annular gasket;
a first adhesive label disposed in overlying relation to said first annular gasket and said first resilient foam biasing pad;
said first adhesive label having a central aperture formed therein that corresponds in diameter with the central aperture formed in said front surface, said first adhesive label central aperture having a center coincident with a longitudinal axis of symmetry of said first conduit;
a first rolling membrane having a first section integral with said first adhesive label, said first section being folded with respect to said first adhesive label and having a rear surface disposed in overlying relation to said first adhesive label and being releasably adhered thereto, said first section having a width greater than the respective common diameters of said first central aperture formed in said front surface of said first rigid latching support card and said first adhesive label central aperture;
said first rolling membrane having a second section that is folded with respect to said first section, said second section having a rear surface disposed in overlying relation to said first section and being releasably adhered thereto;
an adhesive applied to a front suffice of said first rolling membrane second section;
a first pull grip formed integrally with said first rolling membrane second section, said first pull grip having front and rear surfaces that are adhesive-free;
a second rigid latching support card;
said second rigid latching support card having a rear surface adapted to engage a terminal end of a second conduit;
said second rigid latching support card having a front surface having a diameter greater than a diameter of said second conduit;
said second rigid latching support card having a central bore formed therein that is in fluid communication with said terminal end of said second conduit;
said front surface of said second rigid latching support card being centrally apertured said central aperture being the forward extent of said second rigid latching support card central bore;
a second annular gasket of resilient construction positioned on said second rigid latching support card front surface in surrounding relation to said central aperture formed in said second rigid latching support card front surface;
a second resilient foam biasing pad positioned on said second rigid latching support card front surface in surrounding relation to said second annular gasket;
a second adhesive label disposed in overlying relation to said second annular gasket and said second resilient foam biasing pad;
said second adhesive label having a central aperture formed therein that corresponds in diameter with the central aperture formed in said second rigid latching support card front surface, said second adhesive label central aperture having a center coincident with a longitudinal axis of symmetry of said second conduit;
a second rolling membrane having a first section integral with said second adhesive label, said first section being folded with respect to said second adhesive label and having a rear surface disposed in overlying relation to said second adhesive label and being releasably adhered thereto, said second rolling membrane first section having a width greater than the respective diameters of said second rigid latching support card central aperture and said second adhesive label central aperture;
said second rolling membrane having a second section, said second section being folded with respect to said second rolling membrane first section and having a rear surface disposed in overlying relation to said second rolling membrane first section and being releasably adhered thereto;
an adhesive applied to a front surface of said second rolling membrane second section;
a second pull grip formed integrally with said second rolling membrane second section, said second pull grip having front and rear surfaces that are adhesive-free;
whereby said front surface of said second rolling membrane second section and said front surface of said second rolling membrane second section are disposed in abutting relation to one another, in sandwiched relation between said first and second rigid latching support cards, when said terminal end of said first conduit is disposed in abutting relation to said rear surface of said first rigid latching support card and said terminal end of said second conduit is disposed in abutting relation to said rear surface of said second rigid latching support card;
whereby pulling said first and second pull grips in a radial direction away from the common longitudinal axis of said first and second conduits removes said first and second rolling membranes from their sandwiched position between said first and second adhesive labels so that said first and second adhesive labels are urged into abutting relation to one another by the resiliency of said first and second annular gaskets and said first and second resilient foam biasing pads and adhere to one another to thereby join together said first and second rigid latching support cards and said respective terminal ends of said first and second conduits;

whereby said first and second annular gaskets and said first and second resilient foam biasing pads provide a bias that pushes together said first and second adhesive labels, thereby obviating any need for resilient support cards.

22. An apparatus for establishing an aseptic/sterile connection between respective terminal ends of a first and a second conduit where said first and second conduits have a common internal diameter and are positioned along a common longitudinal axis of symmetry, comprising:

a first sanitary fitting having a rigid construction;

said first sanitary fitting having a rear surface adapted to engage a terminal end of a first conduit;

said first sanitary fitting having a front surface having a diameter greater than a diameter of said first conduit;

said first sanitary fitting having a central bore formed therein that is in fluid communication with said terminal end of said first conduit;

said first sanitary fitting front surface being centrally apertured, said first sanitary fitting front surface central aperture being the forward extent of said first conduit central bore;

a first annular ridge formed about the periphery of said front surface central aperture in perpendicular relation to said front surface;

a second annular ridge formed radially outwardly of said first annular ridge, said second annular ridge disposed in perpendicular relation to said first sanitary fitting front surface;

a first annular gasket of resilient construction positioned snugly between said first and second annular ridges;

a third annular ridge formed about the periphery of said first sanitary fitting front surface, said third annular ridge disposed in perpendicular relation to said first sanitary fitting front surface;

a first resilient foam biasing pad disposed snugly between said second annular ridge and said third annular ridge;

a first adhesive label disposed in overlying relation to said front surface of said first annular gasket and said first foam biasing pad;

a first adhesive label central aperture formed in said first adhesive label;

said first sanitary fitting front surface central aperture and said first adhesive label central aperture sharing a common predetermined diameter equal to said inner diameter of said first conduit;

said first sanitary fitting front surface central aperture and said first adhesive label central aperture having their respective centers coincident with said common longitudinal axis of symmetry;

a first rolling membrane formed integrally with said first adhesive label;

a first fold formed in said first rolling membrane to form a first section, said first section having a rear surface disposed in overlying relation to said first adhesive label and being releasably adhered thereto, said first section having a width greater than the common diameter of said respective central apertures formed in said first sanitary fitting front surface and said first adhesive label;

a second fold formed in said first rolling membrane being folded to form a second section, said second section having a rear surface disposed in overlying relation to said first rolling membrane first section and being releasably adhered thereto;

an adhesive applied to a front surface of said first rolling membrane second section;

a first pull grip formed integrally with said first rolling membrane second section, said first pull grip having front and rear surfaces that are adhesive-free;

a second sanitary fitting having a rigid construction;

said second sanitary fitting having a rear surface adapted to engage a terminal end of a second conduit;

said second sanitary fitting having a front surface having a diameter greater than a diameter of said second conduit;

said second sanitary fitting having a central bore formed therein that is in fluid communication with said terminal end of said second conduit;

said second sanitary fitting front surface being centrally apertured, said central aperture being the forward extent of said second conduit central bore;

a first annular ridge formed about the periphery of said second sanitary fitting front surface central aperture in perpendicular relation to said front surface;

a second annular ridge formed radially outwardly of said first annular ridge, said second annular ridge disposed in perpendicular relation to said second sanitary fitting front surface;

a second annular gasket of resilient construction positioned snugly between said first and second annular ridges;

a third annular ridge formed about the periphery of said second sanitary fitting front surface, said third annular ridge disposed in perpendicular relation to said second sanitary fitting front surface;

a second resilient foam biasing pad disposed snugly between said second annular ridge and said third annular ridge;

a second adhesive label disposed in overlying relation to said second sanitary fitting front surface;

a second adhesive label central aperture formed in said second adhesive label;

said second sanitary fitting front surface central aperture and said second adhesive label central aperture sharing a common predetermined diameter equal to said inner diameter of said second conduit;

said second sanitary fitting front surface central aperture and said second adhesive label central aperture having their respective centers coincident with said common longitudinal axis of symmetry;

a second rolling membrane formed integrally with said second adhesive label;

a first fold formed in said second rolling membrane to form a first section, said first section having a rear surface disposed in overlying relation to said second adhesive label and being releasably adhered thereto, said first section having a width greater than the common diameter of said second sanitary fitting front surface central aperture and said second adhesive label central aperture;

a second fold formed in said second rolling membrane to form a second section, said second section having a rear surface disposed in overlying relation to said first section and being releasably adhered thereto;

an adhesive applied to a front surface of said second rolling membrane second section;

a second pull grip formed integrally with said second rolling membrane second section, said second pull grip having front and rear surfaces that are adhesive-free;

whereby said front surface of said first rolling membrane second section and said front surface of said second rolling membrane second section are disposed in abutting relation to one another, in sandwiched relation between said first and second sanitary fittings, when said terminal end of said first conduit is disposed in abutting relation to said rear surface of said first sanitary fitting and said terminal end of said second conduit is disposed in abutting relation to said rear surface of said second sanitary fitting;

whereby pulling said first and second pull grips in a radial direction away from said common longitudinal axis of said first and second conduits removes said first and second rolling membranes from their sandwiched position between said first and second adhesive labels so that said first and second adhesive labels are urged into abutting relation to one another by the resiliency of said first and second annular gaskets and said first and second foam biasing pads and adhere to one another to thereby join together said first and second sanitary fittings and said respective terminal ends of said first and second conduits;

whereby said first and second annular gaskets and said first and second foam biasing pads obviate any need for resilient support cards; and whereby said first, second, and third annular ridges form barriers that bacteria cannot cross.

23. The apparatus of claim 22, further comprising:

a clamp that houses said first sanitary fitting and said second sanitary fitting;

whereby said clamp provides permanent connection between said first and second conduits.

* * * * *